(12) United States Patent
Castaigne et al.

(10) Patent No.: US 9,173,891 B2
(45) Date of Patent: Nov. 3, 2015

(54) TREATMENT OF OVARIAN CANCER USING AN ANTICANCER AGENT CONJUGATED TO AN ANGIOPEP-2 ANALOG

(75) Inventors: Jean-Paul Castaigne, Mont-Royal (CA); Michel Demeule, Beaconsfield (CA); Betty Lawrence, Bolton (CA)

(73) Assignee: Angiochem, Inc., Montreal (CA)

( * ) Notice: Subject to any disclaimer, the term of this patent is extended or adjusted under 35 U.S.C. 154(b) by 259 days.

(21) Appl. No.: 13/265,309

(22) PCT Filed: Apr. 20, 2010

(86) PCT No.: PCT/CA2010/000618
§ 371 (c)(1),
(2), (4) Date: Jan. 30, 2012

(87) PCT Pub. No.: WO2010/121379
PCT Pub. Date: Oct. 28, 2010

(65) Prior Publication Data
US 2012/0122798 A1 May 17, 2012

Related U.S. Application Data

(60) Provisional application No. 61/171,040, filed on Apr. 20, 2009.

(51) Int. Cl.
*A61K 38/04* (2006.01)
*A61K 31/70* (2006.01)
*A61K 31/337* (2006.01)
*A61K 31/475* (2006.01)
*A61K 31/704* (2006.01)
*A61K 38/10* (2006.01)

(52) U.S. Cl.
CPC .............. *A61K 31/70* (2013.01); *A61K 31/337* (2013.01); *A61K 31/475* (2013.01); *A61K 31/704* (2013.01); *A61K 38/10* (2013.01)

(58) Field of Classification Search
CPC ............... C07K 14/8117; A61K 38/00; A61K 47/48246
See application file for complete search history.

(56) References Cited

U.S. PATENT DOCUMENTS

| | | |
|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |
| 6,310,039 B1 | 10/2001 | Kratz |
| 6,316,024 B1 | 11/2001 | Allen et al. |
| 6,348,207 B1 | 2/2002 | Milstein et al. |
| 6,376,648 B2 | 4/2002 | White et al. |
| 6,391,305 B1 | 5/2002 | Feng et al. |
| 6,391,913 B1 | 5/2002 | Page et al. |
| 6,469,047 B1 | 10/2002 | Jackson et al. |

(Continued)

FOREIGN PATENT DOCUMENTS

| | | |
|---|---|---|
| CA | 2283474 | 9/1998 |
| CA | 2525236 A1 | 1/2005 |

(Continued)

OTHER PUBLICATIONS

Michaud et al. (Drug Safety, 23(5):401-428, 2000).*
Rose et al. (Cancer, 64(7):1508-1513, 1989).*
Markman et al. (J. Clin. Oncol., 20(9):2365-2369, 2002).*
Seiden et al. (Gynecol. Oncol., 86:302-310, 2002).*
Kurzrock et al. (European Journal of Cancer including EJC Supplements, 20th EORTC-NCI-AACR Symposium on Molecular Targets and Cancer Therapeutics 6(12): abstract #424, Oct. 2008).*
Demeule et al. (Journal of Pharmacology and Experimental Therapeutics, 324: 1064-1072, Mar. 2008, published online Dec. 21, 2007).*
Li et al. (Cancer Letters, 111: 199-205, 1997).*

(Continued)

*Primary Examiner* — Misook Yu
*Assistant Examiner* — Nelson B Moseley, II
(74) *Attorney, Agent, or Firm* — Clark & Elbing LLP; Kristina Bieker-Brady

(57) ABSTRACT

Ovarian cancer is treated with conjugates of an anticancer agent and an Angiopep-2 polypeptide analog (i.e. a polypeptide comprising an amino acid sequence at least 80% identical to Seq. ID NO:97). Such treatment includes utility in treating metastatic ovarian cancer and in treating patients who have previously exhibited resistance to standard chemotherapeutic agents. Preferred anticancer agents include taxanes while the preferred conjugate is ANG1005, a conjugate comprising three molecules of paclitaxel conjugated to the peptide Angiopep-2.

16 Claims, 8 Drawing Sheets

(56) References Cited

U.S. PATENT DOCUMENTS

| | | |
|---|---|---|
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,271,149 B2 | 9/2007 | Glaesner et al. |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 2003/0129186 A1 | 7/2003 | Beliveau et al. |
| 2003/0170891 A1 | 9/2003 | McSwiggen |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1* | 8/2006 | Beliveau et al. .......... 514/8 |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0039785 A1 | 2/2011 | Beliveau et al. |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2012/0015876 A1 | 1/2012 | Castaigne et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |

FOREIGN PATENT DOCUMENTS

| | | |
|---|---|---|
| CA | 2637893 | 7/2007 |
| CA | 2638034 | 7/2007 |
| CA | 2688344 A1 | 12/2008 |
| CN | 101262890 A | 9/2008 |
| CN | 102406949 A | 4/2012 |
| CN | 102552928 A | 7/2012 |
| CN | 102614105 A | 8/2012 |
| DE | 19953696 | 5/2001 |
| EP | 0393431 | 10/1990 |
| EP | 0495049 B1 | 7/1992 |
| EP | 1982699 A1 | 10/2008 |
| EP | 2333074 A1 | 6/2011 |
| JP | 2007-509977 A | 4/2007 |
| WO | WO 87/05702 | 9/1987 |
| WO | WO 96/31531 | 10/1996 |
| WO | WO 96/35788 | 11/1996 |
| WO | WO 96/39183 | 12/1996 |
| WO | WO 96/40210 | 12/1996 |
| WO | WO 97/33996 | 9/1997 |
| WO | WO-97/40160 A1 | 10/1997 |
| WO | WO 97/40854 | 11/1997 |
| WO | WO-97/40854 A2 | 11/1997 |
| WO | WO 00/01417 | 1/2000 |
| WO | WO 00/71574 | 11/2000 |
| WO | WO 01/30319 | 5/2001 |
| WO | WO 02/33090 | 4/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | WO 2004/060403 | 7/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO 2006/086870 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |
| WO | WO 2007/103515 | 9/2007 |
| WO | WO 2007/113172 | 10/2007 |
| WO | WO 2008/012629 | 1/2008 |
| WO | WO-2008/012629 A2 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO-2009/039188 A1 | 3/2009 |
| WO | WO 2009/046220 | 4/2009 |
| WO | WO 2009/070597 | 6/2009 |
| WO | WO-2009/070597 A2 | 6/2009 |
| WO | WO 2009/079790 | 7/2009 |
| WO | WO 2009/105671 | 8/2009 |
| WO | WO 2009/127072 | 10/2009 |
| WO | WO 2010/043047 | 4/2010 |

(56) References Cited

FOREIGN PATENT DOCUMENTS

| | | |
|---|---|---|
| WO | WO 2010/043049 | 4/2010 |
| WO | WO 2010/063122 | 6/2010 |
| WO | WO 2010/063123 | 6/2010 |
| WO | WO 2010/063124 | 6/2010 |
| WO | WO-2010/063124 A1 | 6/2010 |
| WO | WO 2010/069074 | 6/2010 |
| WO | WO-2010/121379 A1 | 10/2010 |
| WO | WO 2010/142035 | 12/2010 |
| WO | WO-2010/142035 A1 | 12/2010 |
| WO | WO 2011/000095 | 1/2011 |
| WO | WO-2011/008823 A2 | 1/2011 |
| WO | WO 2011/041897 | 4/2011 |
| WO | WO-2011/041897 A1 | 4/2011 |
| WO | WO-2011/063507 A1 | 6/2011 |
| WO | WO-2011/112635 A1 | 9/2011 |
| WO | WO 2011/153642 | 12/2011 |
| WO | WO-2011/153642 A1 | 12/2011 |
| WO | WO 2012/000118 | 1/2012 |
| WO | WO-2012/000118 A1 | 1/2012 |
| WO | WO-2012/006239 A1 | 1/2012 |
| WO | WO 2012/037687 | 3/2012 |
| WO | WO-2012/037687 A1 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |

OTHER PUBLICATIONS

Ballabh et al., "The Blood-Brain Barrier: An Overview Structure, Regulation, and Clinical Implications," *Neurobiol Dis*. 16:1-13 (2004).
Bickel et al., "Delivery of Peptides and Proteins Through the Blood-Brain Barrier," *Adv Drug Deliv Rev*. 46:247-279 (2001).
Boado, "Blood-brain Barrier Transport of Non-viral Gene and RNAi Therapeutics," *Pharm Res*. 24:1772-1787 (2007).
Bork, "Powers and Pitfalls in Sequence Analysis: The 70% Hurdle," *Genome Res*. 10:398-400 (2000).
Bork et al., "Go Hunting in Sequence Databases But Watch Out for the Traps," *Trends Genet*. 12:425-427 (1996).
Brenner, "Errors in Genome Annotation," *Trends Genet*. 15:132-133 (1999).
Castex et al., "2-Pyrrolinodoxorubicin and Its Peptide-vectorized Form Bypass Multidrug Resistance," *Anticancer Drugs*. 15:609-617 (2004).
Coon et al., "Solutol HS 15, Nontoxic Polyoxyethylene Esters of 12-hydroxystearic Acid, Reverses Multidrug Resistance," *Cancer Res*. 51:897-902 (1991).
D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug Chem*. 16:1299-1309 (2005).

Dagenais et al., "Development of an In Situ Mouse Brain Perfusion Model and Its Application to mdr1a P-glycoprotein-deficient Mice," *J Cereb Blood Flow Metab*. 20:381-386 (2000).
Deane et al., "LRP/Amyloid β-Peptide Interaction Mediates Differential Brain Efflux of Aβ Isoforms," *Neuron*. 43:333-344 (2004).
Dehouck et al., "A New Function for the LDL Receptor: Transcytosis of LDL Across the Blood-Brain Barrier," *J Cell Biol*. 138:877-889 (1997).
Dehouck et al., "An Easier, Reproducible, and Mass-production Method to Study the Blood-brain Barrier in Vitro," *J Neurochem*. 54:1798-1801 (1990).
Dehouck et al., "Drug Transfer Across the Blood-Brain Barrier: Correlation Between In Vitro and In Vivo Models," *J Neurochem*. 58:1790-1797 (1992).
Demeule et al., "High Transcytosis of Melanotransferrin (P97) Across the Blood-Brain Barrier," *J Neurochem*. 83:924-933 (2002).
Demeule et al., "Identification and Design of Peptides As a New Drug Delivery System for the Brain," *J Pharmacol Exp Ther*. 324:1064-1072 (2008).
Demeule et al., "Isolation of Endothelial Cells from Brain, Lung, and Kidney: Expression of the Multidrug Resistance P-Glycoprotein Isoforms," *Biochem Biophys Res Commun*. 281:827-834 (2001).
Doerks et al., "Protein Annotation: Detective Work for Function Prediction," *Trends Genet*. 14:248-250 (1998).
Fillebeen et al., "Receptor-Mediated Transcytosis of Lactoferrin Through the Blood-Brain Barrier," *J Biol Chem*. 274:7011-7017 (1999).
Fromm, "P-glycoprotein: A Defense Mechanism Limiting Oral Bioavailability and CNS Accumulation of Drugs," *Int J Clin Pharmacol Ther*. 38:69-74 (2000).
Gelmon, "The Taxoids: Paclitaxel and Docetaxel," *Lancet*. 344:1267-1272 (1994).
Gewirtz, "A Critical Evaluation of the Mechanisms of Action Proposed for the Antitumor Effects of the Anthracycline Antibiotics Adriamycin and Daunorubicin," *Biochem Pharmacol*. 57:727-741 (1999).
Grabb et al., "Neoplastic and Pharmacological Influence on the Permeability of an in vitro Blood-Brain Barrier," *J Neurosurg*. 82:1053-1058 (1995).
Guillot et al., "Angiotensin Peptide Regulation of Bovine Brain Microvessel Endothelial Cell Monolayer Perrneability," *J Cardiovasc Pharmacol*. 18:212-218 (1991).
Gumbleton et al., "Progress and Limitations in the Use of In Vitro Cell Cultures to Serve as a Permeability Screen for the Blood-Brain Barrier," *J Pharm Sci*. 90:1681-1698 (2001).
Hawkins et al., "The Blood-Brain Barrier/Neurovascular Unit in Health and Disease," *Pharmacol Rev*. 57:173-185 (2005).
Hussain et al., "The Mammalian Low-Density Lipoprotein Receptor Family," *Annu Rev Nutr*. 19:141-172 (1999).
Ito et al., "Functional Characterization of the Brain-to-Blood Efflux Clearance of Human Amyloid-β Peptide (1-40) Across the Rat Blood-Brain Barrier," *Neurosci Res*. 56:246-252 (2006).
Ke et al., "Gene Delivery Targeted to the Brain Using an Angiopep-conjugated Polyethyleneglycol-modified Polyamidoamine Dendrimer," *Biomaterials*. 30:6976-6985 (2009).
Kiernan et al., "Fluorescent—Labelled Aprotinin: A New Reagent for the Histochemical Detection of Acid Mucosubstances," *Histochemie*. 34: 77-84 (1973).
Kobayashi et al., "The Protease Inhibitor Bikunin, a Novel Anti-Metastatic Agent," *Biol Chem*. 384:749-754 (2003).
Koo et al., "Differential Expression of Amyloid Precursor Protein mRNAs in Cases of Alzheimer's Disease and in Aged Nonhuman Primates," *Neuron*. 2:97-104 (1990).
Kounnas et al, "LDL Receptor-related Protein, a Multifunctional ApoE Receptor, Binds Secreted Beta-amyloid Precursor Protein and Mediates Its Degradation," *Cell*. 82:331-340 (1995).
Koziara et al., "In Situ Blood-brain harrier Transport of Nanoparticles," *Pharm Res*. 20:1772-1778 (2003).
Kreuter et al., "Apolipoprotein-Mediated Transport of Nanoparticle-Bound Drugs Across the Blood-Brain Barrier," *J Drug Target*. 10:317-325 (2002).
Kreuter et al., "Direct Evidence that Polysorbate-80-coated Poly(Butylcyanoacrylate) Nanoparticles Deliver Drugs to the CNS

(56) References Cited

OTHER PUBLICATIONS

Via Specific Mechanisms Requiring Prior Binding of Drug to the Nanoparticles," *Pharm Res*. 20:409-416 (2003).
Kreuter, "Nanoparticulate Carriers for Drug Delivery to the Brain," *Nanoparticles as Drug Carriers*, Torchilin VP, Imperial College Press, London pp. 527-547 (2006).
Laccabue et al., "A Novel Taxane Active against an Orthotopically Growing Human Glioma Xenograft," *Cancer*. 92:3085-3092 (2001).
Lai et al., "The Critical Component to Establish in vitro BBB Model: Pericyte," *Brain Res Rev*. 50:258-265 (2005).
Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler*. 366:743-748 (1985).
Larsson, "Megalin, an Endocytocic Receptor With Signalling Potential," *Acta Universitatis Upsaliensis Uppsala* 1-60 (2006).
Ma et al., "Cationic Charge-Dependent Hepatic Delivery of Amidated Serum Albumin," *J Control Release*. 102:583-594 (2005).
Marinô et al., "Megalin-Mediated Transcytosis of Thyroglobulin by Thyroid Cells is a Calmodulin-Dependent Process," *Thyroid*. 10:461-469 (2000).
Marinô et al., "Transcytosis of Retinol-Binding Protein Across Renal Proximal Tubule Cells After Megalin (gp 330)-Mediated Endocytosis," *J Am Soc Nephrol*. 12:637-648 (2001).
Martel et al., "Transport of Apolipoproteins E and J at the Blood-Brain Barrier Relevance to Alzheimer's disease," *S.T.P. Pharma Sciences*. 7:28-36 (1997).
Mazel et al., "Doxorubicin-peptide Conjugates Overcome Multidrug Resistance," *Anticancer Drugs*. 12:107-116 (2001).
McCarty, "Cell Biology of the Neurovascular Unit: Implications for Drug Delivery Across the Blood-Brain Barrier," *Assay Drug Dev Technol*. 3:89-95 (2005).
Moestrup et al., "Evidence that Epithelial Glycoprotein 330/Megalin Mediates Uptake of Polybasic Drugs," *J.Clin. Invest*. 96:1404-1413 (1995).
Moore et al., "The Role of Flexible Tethers in Multiple Ligand-receptor Bond Formation Between Curved Surfaces," *Biophys J*. 91:1675-1687 (2006).
Muratovska et al., "Conjugate for Efficient Delivery of Short Interfering RNA (siRNA) Into Mammalian Cells," *FEBS Lett*. 558:63-68 (2004).
Ngo et al., "Computational Complexity; Protein Structure Prediction, and the Levinthal Paradox," *The Protein Folding Problem and Tertiary Structure Prediction* Merz, Jr. And Le Grand, Eds. 491-495 (1994).
Niola et al., "A Plasmid-encoded VEGF siRNA Reduces Glioblastoma Angiogenesis and Its Combination with Interleukin-4 Blocks Tumor Growth in a Xenograft Mouse Model," *Cancer Biol Ther*. 5:174-179 (2006).
Orlando et al., "Identification of the Second Cluster of Ligand-Binding Repeats in Megalin as a Site for Receptor-Ligand Interactions," *Proc Natl Acad Sci*. 94:2368-2373 (1997).
Pan et al., "Efficient Transfer of Receptor-Associated Protein (RAP) Across the Blood-Brain Barrier," *J Cell Sci*. 117:5071-5078 (2004).
Pardridge, "Blood-Brain Barrier Biology and Methodology," *J Neurovirol*. 5:556-569 (1999).
Pardridge, "CNS Drug Design Based on Principles of Blood-Brain Barrier Transport," *J Neurochem*. 70:1781-1792 (1998).
Pardridge, "Drug Targeting to The Brain," *Pharm Res*. 24:1733-1744 (2007).
Peri et al., "D-Glucose as a Regioselectively Addressable Scaffold for Combinatorial Chemistry on Solid Phase," *J Carbohydr Chem*. 22:57-71 (2003).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem*. 279:35037-35046 (2004).
Qu et al., "Carbohydrate-based Micelle Clusters Which Enhance Hydrophobic Drug Bioavailability by Up to 1 Order of Magnitude," *Biomacromolecules*. 7:3452-3459 (2006).

Ramakrishnan, "The Role of P-glycoprotein in the Blood-Brain Barrier," *Einstein Q J Biol Med*. 19:160-165 (2003).
Rawat et al., "Lipid Carriers: A Versatile Delivery Vehicle for Proteins and Peptides," *Yakugaku Zasshi*. 128:269-280 (2008).
Regina et al., "Antitumour Activity of ANG1005, a Conjugate Between Paclitaxel and the New Brain Delivery Vector Angiopep-2," *Br J Pharmacol*. 155:185-197 (2008).
Régina et al., "Differences in Multidrug Resistance Phenotype and Matrix Metalloproteinases Activity Between Endothelial Cells from Normal Brain and Glioma," *J Neurochem*. 84:316-324 (2003).
Scherrmann, "Drug Delivery to Brain Via the Blood-Brain Barrier," *Vascul Pharmacol*. 38:349-354 (2002).
Schinkel, "P-Glycoprotein, A Gatekeeper in the Blood-Brain Barrier," *Adv Drug Deliv Rev*. 36:179-194 (1999).
Seidel et al., "Effects of Trasylol on the Blood-Brain Barrier in Rats," *Naunyn Schmiedebergs Arch Pharmacol*. 284:R73 (1974).
Shibata et al., "Clearance of Alzheimer's Amyloid-$\beta_{1-40}$ Peptide From Brain by LDL Receptor-Related Protein-1 at the Blood-Brain Barrier," *J Clin Invest*. 106:1489-1499:(2000).
Shiiki et al., "Brain Insulin Impairs Amyloid-$\beta$(1-40) Clearance From the Brain," *J Neurosci*. 24:9632-9637 (2004).
Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther*. 258:459-465 (1991).
Skolnick et al., "From Genes to Protein Structure and Function: Novel Applications of Computational Approaches in the Genomic Era," *Trends Biotechnol*. 18:34-39 (2000).
Smith, "Brain Perfusion Systems for Studies of Drug Uptake and Metabolism in the Central Nervous System," *Pharm Biotechnol*. 285-307 (1996).
Smith et al., "The Challenges of Genome Sequence Annotation or 'The Devil is in the Details'," *Nat Biotechnol*. 15:1222-1223 (1997).
Steiniger et al., "Chemotherapy of Glioblastoma in Rats Using Doxorubicin-loaded Nanoparticles," *Int J Cancer*. 109:759-767 (2004).
Tamai et al., "Structure-Internalization Relationship for Adsorptive-Mediated Endocytosis of Basic Peptides at the Blood-Brain Barrier," *J Pharmacol Exp Ther*. 280:410-415 (1997).
Temsamani et al., "Vector-Mediated Drug Delivery to the Brain," *Expert Opin Biol Ther*. 1:773-782 (2001).
Terasaki et al., "New Approaches to in vitro Models of Blood-Brain Barrier Drug Transport," *Drug Discov Today*. 8:944-954 (2003).
Triguero et al., "Capillary Depletion Method for Quantification of Blood-Brain Barrier Transport of Circulating Peptides and Plasma Proteins," *J Neurochem*. 54:1882-1888 (1990).
Turner et al., "RNA Targeting With Peptide Conjugates of Oligonucleotides, siRNA and PNA," *Blood Cells Mol Dis*. 38:1-7 (2007).
Veronese et al., "PEGylation, Successful Approach to Drug Delivery," *Drug Discov Today*. 10:1451-1458 (2005).
Wang et al., "DNA/dendrimer Complexes Mediate Gene Transfer into Murine Cardiac Transplants ex Vivo," *Mol Ther*. 2:602-608 (2000).
Wells, "Additivity of Mutational Effects in Proteins," *Biochemistry*. 29:8509-8517 (1990).
Witt et al., "Peptide Drug Modifications to Enhance Bioavailability and Blood-Brain Barrier Permeability," *Peptides*. 22:2329-2343 (2001).
Xu et al., "In Vitro and in Vivo Evaluation of Actively Targetable Nanoparticles for Paclitaxel Delivery," *Int J Pharm*. 288:361-368 (2005).
Yepes et al., "Tissue-Type Plasminogen Activator Induces Opening of the Blood-Brain Barrier Via the LDL Receptor-Related Protein," *J Clin Invest*. 112:1533-1540 (2003).
Zhang et al., "Intravenous RNA Interference Gene Therapy Targeting the Human Epidermal Growth Factor Receptor Prolongs Survival in Intracranial Brain Cancer," *Clin Cancer Res*. 10:3667-3677 (2004).
Zhang et al., "Silencing the Epidermal Growth Factor Receptor Gene with RNAi may be Developed as a Potential Therapy for Non Small Cell Lung Cancer," *Genet Vaccines Ther*. 3.5 (2005).

(56) References Cited

OTHER PUBLICATIONS

Zhang et al., "siRNA-containing Liposomes Modified with Polyarginine Effectively Silence the Targeted Gene," *J Control Release*. 112:229-239 (2006).
Zlokovic et al., "Glycoprotein 330/Megalin: Probable Role in Receptor-mediated Transport of Apolipoprotein J Alone and in a Complex With Alzheimer Disease Amyloid β at the Blood-Brain and Blood-Cerebrospinal Fluid Barriers," *Proc Natl Aced Sci U S A*. 93:4229-4234 (1996).
U.S. Appl. No. 12/601,803, filed Nov. 24, 2009, Beliveau et al.
U.S. Appl. No. 12/632,557, filed Dec. 7, 2009, Castaigne et al.
Arpicco et al., "New Coupling Reagents for the Preparation of Disulfide Cross-Linked Conjugates with Increased Stability," *Bioconjugate Chem*. 8:327-337 (1997).
Banks, "Leptin Transport Across the Blood-Brain Barrier: Implications for the Cause and Treatment of Obesity," *Curr. Pharm. Des*. 7:125-133 (2001).
Banks, "The Blood-Brain Barrier as a Cause of Obesity," *Curr. Pharm. Des*. 14:1606-1614 (2008).
Bicamumpaka et al., "In Vitro Cytotoxicity of Paclitaxel-Transferrin Conjugate on H69 Cells," *Oncol. Rep*. 5:1381-1383 (1998).
Demeule et al, "Drug Transport to the Brain: Key Roles for the Efflux Pump P-Glycoprotein in the Blood-Brain Barrier," *Vascul. Pharmacol*. 38:339-348 (2002).
Dooley et al., "An All D-amino Acid Opioid Peptide with Central Analgesic Activity from a Combinatorial Library," *Science* 266: 2019-2022 (1994).
Eigenbrot et al., "X-Ray Structure of Glial Cell-Derived Neurotrophic Factor at 1.9 A Resolution and Implications for Receptor Binding," *Nat. Struct. Biol*. 4:435-438 (1997).
Gabius et al., "Targeting of Neoglycoprotein-Drug Conjugates to Cultured Human Embryonal Carcinoma Cells,"*J. Cancer Res. Clin. Oncol*. 113:126-130 (1987).
Gottschalk et al., "Protein Self-Association in Solution: The Bovine Pancreatic Trypsin Inhibitor Decamer," *Biophys. J*. 84: 3941-3958 (2003).
Harkavyi et al., "Glucagon-Like Peptide 1 Receptor Stimulation Reverses Key Deficits in Distinct Rodent Models of Parkinson's Disease," *J. Neuroinflammation*. 5:19 (2008) (pp. 1-9).
Kalra, "Central Leptin Insufficiency Syndrome: An Interactive Etiology for Obesity, Metabolic and Neural Diseases and for Designing New Therapeutic Interventions," *Peptides* 29:127-138 (2008).
Karyekar et al., "Zonula Occludens Toxin Increases the Permeability of Molecular Weight Markers and Chemotherapeutic Agents Across the Bovine Brain Microvessel Endothelial Cells," *J. Pharm. Sci*. 92:414-423 (2003).
Kirsch et al., "Anti-Angiogenic Treatment Strategies for Malignant Brain Tumors," *J. Neurooncol*. 50:149-163 (2000).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem*. 9:72-86 (1998).
Saito et al., "Drug Delivery Strategy Utilizing Conjugation Via Reversible Disulfide Linkages: Role and Site of Cellular Reducing Activities," *Adv. Drug. Deliv. Rev*. 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther*. 16:1805-1812 (2008) (pp. 1-18).
Uekita et al., "Cytoplasmic Tail-Dependent Internalization of Membrane-Type 1 Matrix Metalloproteinase is Important for its Invasion-Promoting Activity," *J. Cell. Biol*. 155:1345-1356 (2001).
Uekita et al., "Membrane-Type 1 Matrix Metalloproteinase Cytoplasmic Tail-Binding Protein-1 is a New Member of the Cupin Superfamily. A Possible Multifunctiona Protein Acting as an Invasion Suppressor Down-Regulated in Tumors," *J. Biol. Chem*. 279:12734-12743 (2004).
Akhtar et al., "Nonviral Delivery of Synthetic siRNAs in Vivo," *J. Clin. Invest*. 117: 3623-3632 (2007).
Anonymous, "Blood-Brain Barrier Tackled," <http:www.ecancermedicalscience.com/news-insider-news.asp?itemld=326> Oct. 22, 2008.
Bertrand et al., "Transport Characteristics of a Novel Peptide Platform for CNS Therapeutics," *J. Cell Mol. Med*. published online Oct. 10, 2009.
Boules et al., "Bioactive Analogs of Neurotensin: Focus on CNS Effects," *Peptides* 27: 2523-2533 (2006).
Chari, "Targeted Cancer Therapy: Conferring Specificity to Cytotoxic Drugs," *Acc. Chem. Res*. 41:98-107 (2008).
Ché et al., "New Angiopep-Modified Doxorubicin (ANG1007) and Etoposide (ANG1009) Chemotherapeutics with Increased Brain Penetration," *J. Med. Chem*. 53: 2814-2824 (2010).
Demeule et al., "Involvement of the Low-Density Lipoprotein Receptor-Related Protein in the Transcytosis of the Brain Delivery Vector Angiopep-2," *J. Neurochem*. 106: 1534-1544 (2008).
Garsky et al., "The Synthesis of a Prodrug of Doxorubicin Designed to Provide Reduced Systemic Toxicity and Greater Target Efficacy," *J. Med. Chem*. 44: 4216-4224 (2001).
Huang et al., "Targeting Delivery of Paclitaxel into Tumor Cells via Somatostatin Receptor Endocytosis," *Chem. Biol*. 7: 453-461 (2000).
Kilic et al., "Intravenous TAT-GDNF is Protective after Focal Cerebral Ischemia in Mice," *Stroke* 34: 1304-1310 (2003).
Kumar et al., "Transvascular Delivery of Small Interfering RNA to the Central Nervous System," *Nature* 448: 39-43 (2007).
Rouselle et al., "New Advances in the Transport of Doxorubicin through the Blood-Brain Barrier by a Peptide Vector-Mediated Strategy," *Mol. Pharmacol*. 57: 679-686 (2000).
Takei et al., "A Small Interfering RNA Targeting Vascular Endothelial Growth Factor as Cancer Therapeutics," *Cancer Res*. 64: 3365-3370 (2004).
Trail et al., "Cure of Xenografted Human Carcinomas by BR96-Doxorubicin Immunoconjugates," *Science* 261:212-215 (1993).
U.S. Appl. No. 61/546,851, filed Oct. 13, 2011, Demeule et al.
Grimm et al., "Ten Year Biochemical Outcomes Following 125-Iodine Monotherapy for Early Stage Prostate Cancer." *Int. J. Rad. Oncol. Biol. Phys*. 48:146-147 (2000).
Kurzrock et al., "ANGI005: Results of a Phase I study in patients with advanced solid tumors and metastatic brain cancer" Poster B168, ACCR/NCl/EORTC Annual Meeting, 2009.
Mathupala, "Delivery of Small-interfering RNA (siRNA) to the Brain," *Exp. Opin. Ther. Pat*. 19: 137-140, (2009).
Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata* L., using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans*. 35:811-815, (2007).
Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet*. 118:31-37 (2010).
International Search Report and Written Opinion of the International Search Authority for Application No. PCT/CA2010/000618, dated Aug. 4, 2010.
U.S. Appl. No. 61/138,375, Beliveau et al.
Author manuscript of Hein et al., "Click chemistry, a powerful tool for pharmaceutical sciences," published in final edited form as: Pharm Res. 25(10):2216-2230 (2008).
Author manuscript of Howes et al., "Rapid induction of therapeutic hypothermia using convective-immersion surface cooling: Safety, efficacy and outcomes," published in final edited form as: Resuscitation. 81:388-392 (2010).
Belkin et al., "Matrix-dependent proteolysis of surface transglutaminase by membrane-type metalloproteinase regulates cancer cell adhesion and locomotion," J Biol Chem. 276(21):18415-18422 (2001).

(56) References Cited

OTHER PUBLICATIONS

Boado et al., "GDNF fusion protein for targeted-drug delivery across the human blood-b.-am barrier," Biotechnoi Bioeng. 100(2).387-96 (2008).
Brady et al. "Drug design. Refelections on a peptide." Nature. 368(6473):692-693 (1994).
Buvanendran et al., "Recent advances in nonopioid analgesics for acute pain management," Tech Reg Anestii Pain Man. 11(1):19-26 (2007).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmacol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Declaration of Michel Demeule in European Patent Application No. 11010125 dated Sep. 24, 2012 (4 pages).
Demuie et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
DeWitt et al., "'Diversomers': an approach to nonpeptide, nonoligomeric chemi al diverstiy," Proc Natl Acad Sci U S A. 90(15):6909-6913 (1993).
English Translation of Search Report for Chinese Application No. 2010/80027564.4, dated Oct. 23, 2012.
Erb et al., "Recursive deconvolution of combinatorial chemical libraries," Proc Natl Acad Sci U S A. 91(24):11422-11426 (1994).
Evans et al., "Design of nonpeptidal ligands for a peptide receptor: Cholecystokinin antagonists," J Med Chem. 30(7):1229-1239 (1987).
Fauchere et al., "Association with HeLa cells of *Campylobacter jejuni* and *Campylobacter coli* isolated from human feces," Infect Immun. 54(2):283-287 (1986).
Fioretti et al., "Aprotinin-like isoinhibitors in bovine organs," Biol Chem Hoppe Seyler. 369 Suppl:37-42 (1988).
Fodor et al., "Multiplexed biochemical assays with biological chips," Nature. 364(6437):555-556 (1993).
Furuta et al., "Structure-antinociceptive activity studies with neurotensin," Br J Pharmacol. 83(1):43-48 (1984).
Gabathuler, "Approcaches to the transport therapeutic drugs across the blood-brain barrier to treat brain diseases," Neurobiol Dir.. 37(1):48-57 (2010).
Gallop et al.. "Applications of combinatorial technologies to drug discovery. 1. Background and peptide combinatorial libraries," J Med Chem. 37(9):1233-1251 (1994).
Halab et al., "Design, synthesis, and conformational analysis of azacycloalkane amino acids as conformationally constrained probes for mimicry cf peptide secondary structures," Biopoiymers. 55(2):101-122 (2000).

Hanessian et al., "Synthesis of (4S)-hydroxymethy!-(2R)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpressions of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproternase and activation of progelatinase A in human osteoarthritic cartilage," Am .J Pathol. 151(1):245-256 (1997).
International Preliminary Report on Patentability for International Application No. PCT/CA2010/000618, issued Oct. 25, 2011 (7 pages).
Itoh et al., "MT1-MMP: a potent modifier of pericellular microenvironment," J Cell Physiol. 206(1):1-8 (2006).
J.E. Lachowicz et al., "Analgesic properties of a novel brain-penetrant Angiopep-2-neurotensin derivative (ANG2002) for treating chronic pain," *Program No. 173.28/AA9 2012 Neuroscience Meeting Planner*, New Orleans, LA: Society for Neuroscience (2012).
Jameson et al., "A rationally designed CD4 analogue inhibits experimental allergic encephalomyelitis," Nature. 368(6473):744-746 (1994).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and ceiecoxib for newly diagnosed glioblastoma in adults," Neuro Oncol. 10(3):300-308 (2008).
Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 5P(11):691-7 (1999).
Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Moase et al., "Anti-MUC-1 immunoliposomal doxorubicin in the treatment of murine models of metastatic breast cancer," Biochem Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).

(56) References Cited

OTHER PUBLICATIONS

Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Office Action for Chinese Patent Application No. 201080027564.4, mailed Oct. 31, 2012 (8 pages).
Office Action for Chinese Patent Application No. 201080027564.4, mailed Sep. 4, 2013 (9 pages).
Pardridge et ai. "Combined use of carboxyl-directed protein pegyiation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Acad Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo at al. "Constrained peptides: models of bioactive peptides and protein substructures," Annu Rev Biochem. 61:387-418(1992).
Rudikoff at al., "Single amino acid substitution altering antigen-binding specificity," Proc Natl Acad Sci USA. 79:1979-83 (1982).
Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Search Report for Chinese Patent Application No. 201080027564.4, dated Oct. 23, 2012 (4 pages).
Shao et al., "Angiopep-2 modified PE-PEG based polymeric micelles for amphotericin B delivery targeted to the brain," J Control Release. 147(1):118-26 (2010).
Spatola et al., "Structure-activity relationships of enkephalins containing serially replaced thiomethylene amide bond surrogates," Life Sci. 38(14):1243-9 (1986).
Supplementary European Search Report for International Application No. PCT/CA2010000889, dated Feb. 26, 2013 (10 pages).
Svenson et al., "Dendrimers in biomedical applications—reflections on the field," Adv Drug Deliv Rev. 57(15):2106-2129 (2005).
UniProtKB Entry P08103 (MDR1_HUMAN), "Multidrug resistance proteins 1(EC 3.63.44)(ATP-binding cassette DE subfamily B member 1) (P-glycoprotein 1) (CD243 antigen)," Sep. 18, 2013 (16 pages).
Wang et al., "Polyamidoamine dendrimers with -a modified Pentaerythritoi core having high efficiency and low cytotoxicity as gene carriers," Biomacromolecules. 10(3):617-622 (2009).

Wang et al., "Synthesis and antinociceptive effects of endomorphin-1 analogs with C-terminal linked by oligoarginine," Peptides. 32(2):293-9 (2011).
Williamson et al., "Expression and purification of recombinant neurotensin in *Escherichia coli*," Protein Expr Purif. 19(2):271-5 (2000).
Yano et al., "Simultaneous activation of two different receptor systems by enkephalin/neurotensin conjugates having spacer chains of various lengths," Eur J Pharm Sci. 7:41-48 (1998).
Zhai et al. "Expression of membrane type 1 matrix metalloproteinase is associated with cervical carcinoma progression and invasion," Cancer Res. 65(15):6543-6550 (2005).
Zhang et al. "In vitro gene delivery using polyamidoamine dendrimers with a trimesyl core," Biomacromolecules. 6(1):341-350 (2005).
U.S. Appl. No. 61/546,851, filed Oct. 13, 2011, Demuele et al.
Barakat et al., "Modulation of p-glycoprotein function by caveolin-1 phosphorylation," J Neurochem. 101(1):1-8 (2007).
Becker, "Putative antigenic domains in glycoprotein G of rabies virus: is the RGK sequence involved in virus adsorption to cellular receptors?," Virus Genes. 3(3):277-84 (1990).
Chari, R., "Targeted Cancer Therapy: Conferring Specifcity to Cytotoxic Drugs," Acc. Chem. Res. 41:98-107 (2008).
Ché et al., "New Angiopep-modified doxorubicin (ANG1007) and etoposide (ANG 1009) chemotherapeutics with increased brain penetration'" J Med Chem. 53(7):2814-24 (2010).
Demeule et al., "Involvement of the low-density lipoprotein receptor-related protein in the transcytosis of the brain delivery vector angiopep-2," J Neurochem. 106(4):1534-44 (2008).
Huang et al., "Targeting delivery of paclitaxel into tumor cells via somatostatin receptor endocytosis," Chem Biol. 7(7):453-61 (2000).
Jodoin et al., "P-glycoprotein in blood-brain barrier endothelial cells: interaction and oligomerization with caveolins," J Neurochem. 87(4):1010-23 (2003).
Kirsch et al., "Anti-angiogenic treatment strategies for malignant brain tumors," J Neurooncol. 50(1-2):149-63 (2000).
Kurzrock et al., "ANG1005: Results of a Phase I study in patients with advanced solid tumors and metastatic brain cancer," Poster B168, ACCR/NCI/EORTC Annual Meeting (2009) (2 pages).
Rousselle et al., "New Advances in the Transport of Doxorubicin through the Blood-Brain Barrier by a Peptide Vector-Mediated Strategy," Mol. Pharmacol. 57:679-686 (2000).
Office Action for Japanese Patent Application No. 2011-531314, dated May 7, 2014 (15 pages).
Office Action for Chinese Patent Application No. 2010800275644, dated May 7, 2014 (4 pages).
Régina et al., "Antitumour activity of ANG1005, a conjugate between paclitaxel and the new brain delivery vector Angiopep-2," Br J Pharmacol. 155(2):185-97 (2008).
Castaigne et al., "425 Poster ANG1005: Preliminary clinical safety and tolerability in patients with recurrent malignant glioma," Eur J Cancer. 6(12):133-134 (2008).
Kurzrock et al., "424 Poster ANG1005, an Angiopep-2/paclitaxel conjugate: the first clinical trial in patients with advanced cancer and brain metastases: Preliminary safety and tolerability data," Eur J Cancer. 6(12):133 (2008).
Gabathuler et al., "117 Poster ANG1005, Paclitaxel conjugated to the angiopep brain transport vector for the treatment of brain cancer: preclinical studies," Eur J Cancer. 6(12):38-9 (2008).
Gabathuler et al., "147 Poster A new Taxol delivery system for the treatment of brain primary or metastatic tumors," Eur J Cancer. 4(12):47-8 (2006).
Office Action for Japanese Patent Application No. 2012-505012 dated May 27, 2014 (5 pages).
Office Action for Russian Patent Application No. 2010137915, mailed Jul. 9, 2014 (4 pages).
International Search Report and Witten Opinion for International Patent Application No. PCT/CA2014/050522, mailed Aug. 11, 2014 (17 pages).
Office Action and its English Translation for Russian Application No. 2011146654, mailed Apr. 22, 2014 (5 pages).

* cited by examiner

TREATMENT OF OVARIAN CANCER USING AN ANTICANCER AGENT CONJUGATED TO AN ANGIOPEP-2 ANALOG

CROSS-REFERENCE TO RELATED APPLICATIONS

This application is the U.S. national stage filing under 35 U.S.C. §371 of International Patent Application No. PCT/CA2010/000618, filed Apr. 20, 2010, which claims the benefit of the filing date of U.S. Patent Application No. 61/171,040, filed Apr. 20, 2009.

BACKGROUND OF THE INVENTION

The invention relates to methods for the treatment of ovarian cancer.

Ovarian cancer is a serious health problem; deaths from ovarian cancer in 2008 in the United States were estimated by the National Cancer Institute to be over 15,000, with over 21,000 new cases annually. It is the leading cause of deaths from gynecologic cancers and the fifth most common cause of cancer deaths in women. Based on these numbers, it is estimated that women have a lifetime risk of 1.39% of developing ovarian cancer.

Ovarian cancer is difficult to diagnose early, as the early symptoms are often non-specific for the disease. Thus, only 19% of ovarian cancers are diagnosed before the cancer has spread from the ovaries; indeed, ⅔ of diagnoses occur only occur after the cancer has metastasized to distant locations in the body. Once the cancer has metastasized, the five-year relative survival rate (as compared to the population as a whole) is only 30.6%.

For these reasons, more effective treatments for ovarian cancer, especially those who have metastatic cancer, are needed.

SUMMARY OF THE INVENTION

We have discovered that metastatic ovarian cancer is successfully treated by administration of ANG1005, a therapeutic which includes three molecules of paclitaxel conjugated to the peptide Angiopep-2 (SEQ ID NO:97). This conjugate is able to treat metastatic cancer having metastases both outside and inside the brain, even where the patient is not responsive to standard chemotherapeutic agents. Because ANG1005 is effectively targeted to the cancer cells, it can, in certain cases, be administered at lower equivalent doses than paclitaxel by itself and retain efficacy. Likewise, because the conjugated paclitaxel of ANG1005 can be less toxic than the unconjugated agent, ANG1005 may also be administered in higher doses than paclitaxel alone and exhibit fewer side effects.

On the basis of this discovery, the invention features a method of treating a patient (e.g., a human) having cancer originating from the ovary (e.g., an ovarian epithelial carcinoma or ovarian adenocarcinoma, or metastatic form thereof). The method includes administering to the patient an effective amount of a conjugate including (a) an anticancer agent, and (b) a polypeptide including an amino acid sequence substantially identical to a polypeptide including the amino acid sequence of any of SEQ ID NOS:1-105 and 107-116 (e.g., SEQ ID NO:97), a modified form thereof (e.g., as described herein), or a fragment thereof, where the polypeptide, modified form, or fragment is conjugated to the anticancer agent. In certain embodiments, the anticancer agent is selected from the group consisting of paclitaxel, vinblastine, vincristine, etoposide, doxorubicin, cyclophosphamide, taxotere, melphalan, and chlorambucil. In particular embodiments, the anticancer agent is paclitaxel. In certain embodiments, the polypeptide includes an amino acid sequence at least 70%, 75%, 80%, 85%, 90%, 95%, or 100% identical to the sequence of SEQ ID NO:97. The polypeptide may have The conjugate may be administered in a dosage of about 1, 10, 25, 50, 100, 150, 200, 250, 300, 400, 500, 600, 700, 800, 900, 1000, 1200, 1400, 1600, 1800, 2000, 2500, or 3000 mg/m$^2$, or any range between these numbers. In certain embodiments, the dosage is between 100 mg/m$^2$ and 2000 mg/m$^2$ or between 300 mg/m$^2$ and 1000 mg/m$^2$. The conjugate may be administered by any means known in the art, e.g., intravenously, orally, intraarterially, intranasally, intraperitoneally, intramuscularly, subcutaneously, transdermally, or per os to the patient.

The ovarian cancer may be in any stage (e.g., Stage IA, IB, IC, IIA, IIB, IIC, IIIA, IIIB, IIIC, or IV) or any morphology grade (e.g., Grade 1, Grade 2, or Grade 3) as described herein. The cancer may be in one or both ovaries. The cancer may be confined to the interior of the ovary, or may appear on the outer surface of the ovary. In certain embodiments, cancer cells are found in uterus, fallopian tubes, or both. In other embodiments, the cancer has spread to pelvic organs such as the colon, bladder, or rectum. In other embodiments, cancer cells are found in the abdomen (e.g., visible to the naked eye (e.g., larger or smaller than 2 cm across), or visible only under a microscope). The cancer may also have metastasized to the lining of the abdomen or pelvis (peritoneum), organs of the abdomen such as the bowel, bladder, uterus, liver and lungs, or to the brain. The cancer may have metastasized to at least one location outside the ovary (e.g., to the brain, lung, or both). In certain embodiments, the cancer is in the lymph system. In certain embodiments, the patient has at least one metastasis outside the brain, lung, liver, kidney, or eye.

In particular embodiments, the cancer may be drug resistant or include drug resistant cells (e.g., cells that expresses MDR1). The cancer may be or may include cells that are resistant to any chemotherapeutic agent including paclitaxel, carboplatin, cisplatin, doxorubicin, topotecan, gemcitabine, docetaxel, a taxane derivative, or any agent described herein.

In other embodiments, the method includes administration of a second anticancer therapy (e.g., any therapy described herein). In certain embodiments, the patient may have previously received another chemotherapeutic agent (e.g., paclitaxel, a platinum agent such as carboplatin, cisplatin, doxorubicin, topotecan, gemcitabine, docetaxel, or any agent described herein) and may optionally be drug resistant with respect to that therapeutic. In particular embodiments, the patient previously received combination carboplatin-paclitaxel therapy.

The patient may also have risk factors for developing ovarian cancer (e.g., any risk factor described herein).

In any of the above embodiments, the polypeptide may be of any length, for example, at least 6, 7, 8, 9, 10, 11, 12, 13, 14, 15, 16, 17, 18, 19, 20, 21, 25, 35, 50, 75, 100, 200, or 500 amino acids. In certain embodiments, the polypeptide is 10 to 50 amino acids in length. The conjugate may be substantially pure. The polypeptide may be produced by recombinant genetic technology or chemical synthesis. The conjugate can be formulated with a pharmaceutically acceptable carrier.

The polypeptide may include an amino acid sequence having the formula:

$$X1\text{-}X2\text{-}X3\text{-}X4\text{-}X5\text{-}X6\text{-}X7\text{-}X8\text{-}X9\text{-}X10\text{-}X11\text{-}X12\text{-}X13\text{-}X14\text{-}X15\text{-}X16\text{-}X17\text{-}X18\text{-}X19$$

where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both.

In certain embodiments of any of the above aspects, the polypeptide is modified (e.g., as described herein). The polypeptide may be amidated, acetylated, or both. Such modifications to polypeptides may be at the amino or carboxy terminus of the polypeptide. The conjugates of the invention may also include peptidomimetics of any of the polypeptides described herein. The polypeptide may be in a multimeric form, for example, dimeric form (e.g., formed by disulfide bonding through cysteine residues).

In certain embodiments, the polypeptide has an amino acid sequence described herein with at least one amino acid substitution (e.g., 2, 3, 4, 5, 6, 7, 8, 9, 10, 11, or 12 substitutions). The polypeptide may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. The amino acid substitution(s) may be conservative or non-conservative. For example, the polypeptide may have an arginine at one, two, or three of the positions corresponding to positions 1, 10, and 15 of the amino acid sequence of any of SEQ ID NO:1, Angiopep-1, Angiopep-2, Angiopep-3, Angiopep-4a, Angiopep-4b, Angiopep-5, Angiopep-6, and Angiopep-7.

In any of the above aspects, the conjugate may specifically exclude a polypeptide including or consisting of any of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, the polypeptides and conjugates of the invention exclude the polypeptides of SEQ ID NOS:102, 103, 104, and 105.

In some embodiments, the amino acid sequence has at least 35%, 40%, 50%, 60%, 65%, 70%, 75%, 80%, 85%, 90%, or 95% identity to an amino acid sequence selected from the group consisting of SEQ ID NOS:1-105 and 107-116, or a functional derivative thereof. In certain embodiments, the amino acid sequence has at least 35%, 40%, 50%, 60%, 65%, 70%, 75%, 80%, 85%, 90%, or 95% identity to an amino acid sequence selected from the group consisting of Angiopep-2 (SEQ ID NO:97), Angiopep-4b, Angiopep-5, Angiopep-6, and Angiopep-7 (SEQ ID NOS:109-116). In still other embodiments, the amino acid sequence has at least 35%, 40%, 50%, 60%, 65%, 70%, 75%, 80%, 85%, 90%, or 95% identity to an amino acid sequence of Angiopep-2 (SEQ ID NO:97).

In some embodiments, the amino acid sequence comprises the amino acid sequence selected from the group consisting of SEQ ID NOS:1-105 and 107-116, or a functional derivative thereof. In certain embodiments, the amino acid sequence is that of Angiopep-2 (SEQ ID NO:97), Angiopep-4b, Angiopep-5, Angiopep-6, or Angiopep-7 (SEQ ID NOS:109-112).

In still other embodiments, the amino acid sequence consists of the amino acid sequence selected from the group consisting of SEQ ID NOS:1-105 and 107-116, or a functional derivative thereof. In certain embodiments, the amino acid sequence is that of Angiopep-2 (SEQ ID NO:97), Angiopep-4b, Angiopep-5, Angiopep-6, or Angiopep-7 (SEQ ID NOS:109-112).

By "patient" is meant treating a human or non-human animal (e.g., a mammal).

By "treating" is meant ameliorating at least one symptom of a condition or disease in a subject having the condition or disease (e.g., a subject diagnosed with a metabolic disorder), as compared with an equivalent untreated control. Such reduction in the symptom (e.g., a reduction in blood glucose levels) is at least 5%, 10%, 20%, 40%, 50%, 60%, 80%, 90%, 95%, or 100%, as measured by any standard technique.

By "conjugate" is meant a polypeptide (e.g., those described herein) linked to an anticancer agent. The conjugation may be chemical in nature, such as via a linker, or genetic in nature for example by recombinant genetic technology.

By "an effective amount" is meant an amount of a compound required to treat or reduce ovarian cancer in a clinically relevant manner. For example, a sufficient amount of an active compound used to practice the present invention for therapeutic treatment of ovarian cancer depends upon the manner of administration, the age, body weight, and extent of the cancer. Ultimately, the prescribers will decide the appropriate amount and dosage regimen.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of an analogs which are identical or similar to amino acids of the original polypeptide. The gaps may include no amino acids, one or more amino acids which are not identical or similar to the original polypeptide. Biologically active analogs of the vectors (polypeptides) of the invention are encompassed herewith. Percent identity may be determined, for example, with n algorithm GAP, BESTFIT, or FASTA in the Wisconsin Genetics Software Package Release 7.0, using default gap weights.

By "fragment" is meant a polypeptide originating from a portion of an original or parent sequence or from an analogue of said parent sequence. Fragments encompass polypeptides having truncations of one or more amino acids, wherein the truncation may originate from the amino terminus (N-terminus), carboxy terminus (C-terminus), or from the interior of the protein. A fragment may include the same sequence as the corresponding portion of the original sequence. Functional fragments of the vector (polypeptide) described herein are encompassed by the invention. Fragments may be at least 5 (e.g., at least 5, 6, 7, 8, 9, 10, 11, 12, 13, 14, 15, 16, 17, 18, 19, 20, 21, 22, 23, 25, 28, 30, 35, 40, 45, 50, 60, 75, 100, or 150) amino acids. Fragments of the invention may include, for example, a polypeptide of 7, 8, 9 or 10 amino acids to 18 amino acids. Fragments may contain any of the modifications described herein (e.g., acetylation, amidation, amino acid substitutions).

By a "drug resistant" cancer is meant a cancer that does not respond, or exhibits a decreased response to, one or more chemotherapeutic agents (e.g., any agent described herein).

A cancer "determined to be drug resistant" is meant that the cancer is drug resistant, based on unresponsiveness or decreased responsiveness to a chemotherapeutic agent, or is predicted to be drug resistant based on a prognostic assay (e.g., a gene expression assay).

Other features and advantages of the invention will be apparent from the following Detailed Description, the drawings, and the claims.

DETAILED DESCRIPTION

We have discovered that administration of a peptide-drug-conjugate, as exemplified by ANG1005 (FIG. 1), is capable of treating ovarian cancer in a patient, and, in particular, is able to dramatically shrink metastatic tumors, both those within the brain, as well as those outside the brain (e.g., in the lung) of the patient following only two treatments with ANG1005. Indeed, this particular patient's cancer appeared resistant to standard chemotherapeutics including docetaxel, carboplatin, gemcitabine, topotecan, and doxorubicin, as the patient's cancer continued to progress even after receiving these agents. Because ovarian cancer, particularly metastatic ovarian cancer, has proven to be difficult to treat effectively, and given that such cancers often develop resistance to standard therapies, there is a need for therapeutics and therapeutic regimens capable of treating cancers originating from the ovary, particularly where the cancer has metastasized.

Conjugate Treatment in a Patient Suffering from Ovarian Cancer

A 73-year-old patient diagnosed with metastatic ovarian cancer was selected for participation in a clinical trial of ANG1005. The patient was originally diagnosed in November 2006 with ovarian cancer. Prior to the clinical trial, the patient had received treatment from January 2007 through April 2007 with Taxotere® (docetaxel) and carboplatin. From February 2008 to March 2008, the patient received a combination of Gemzar® (gemcitabine) and Hycamtin® (topotecan). The patient was again given a combination of Taxotere® (docetaxel) and carboplatin from March 2008 until July 2008. In November 2008, the patient was administered Doxil® (doxorubicin). As the patient's cancer continued to progress even upon administration of these agents, the cancer appeared resistance to these agents.

Figures 2A, 2B:
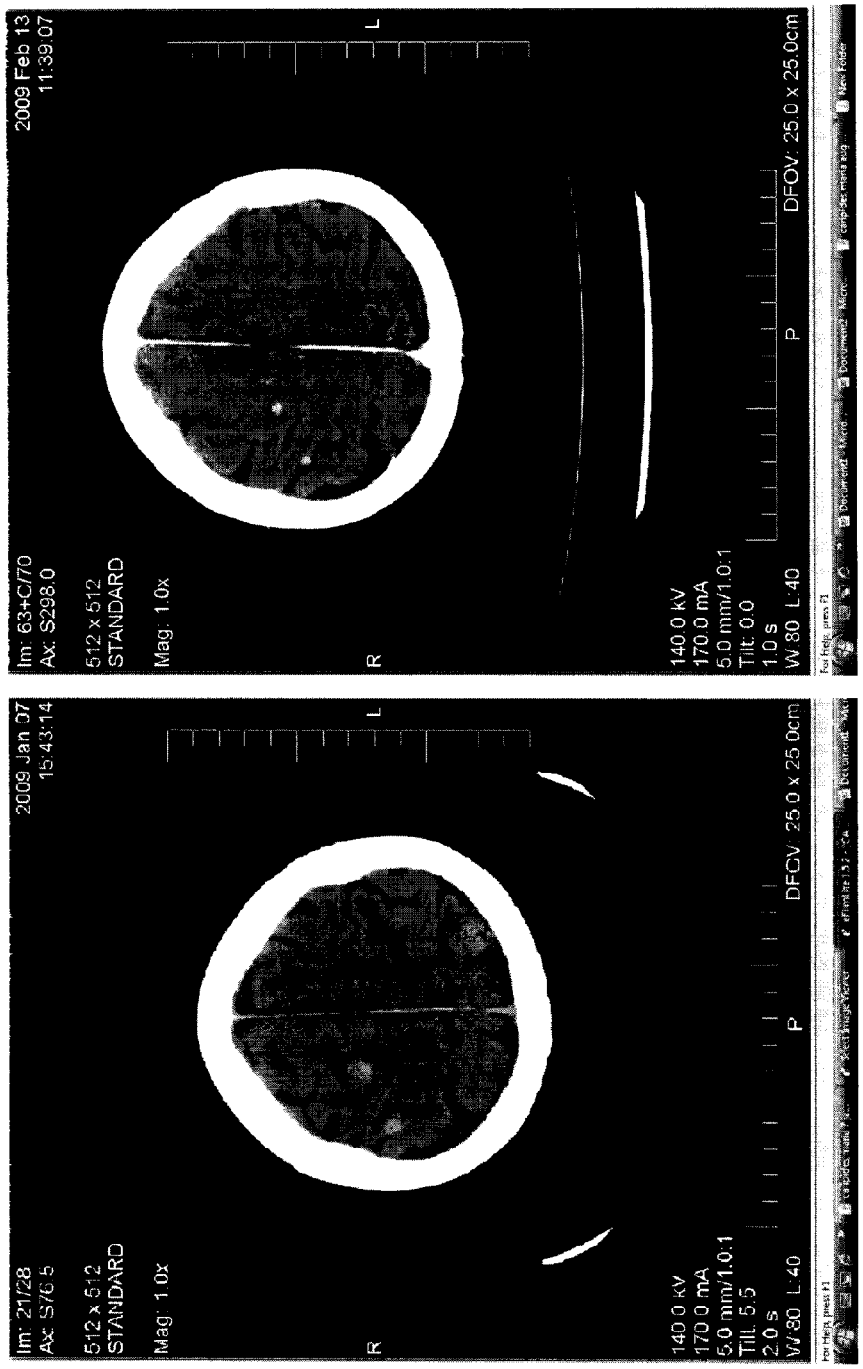
FIGS. 2A and 2B are images showing a CT scan of the patient's brain prior to (FIG. 2A) and following (FIG. 2B) treatment with ANG1005.
Figures 3A, 3B:
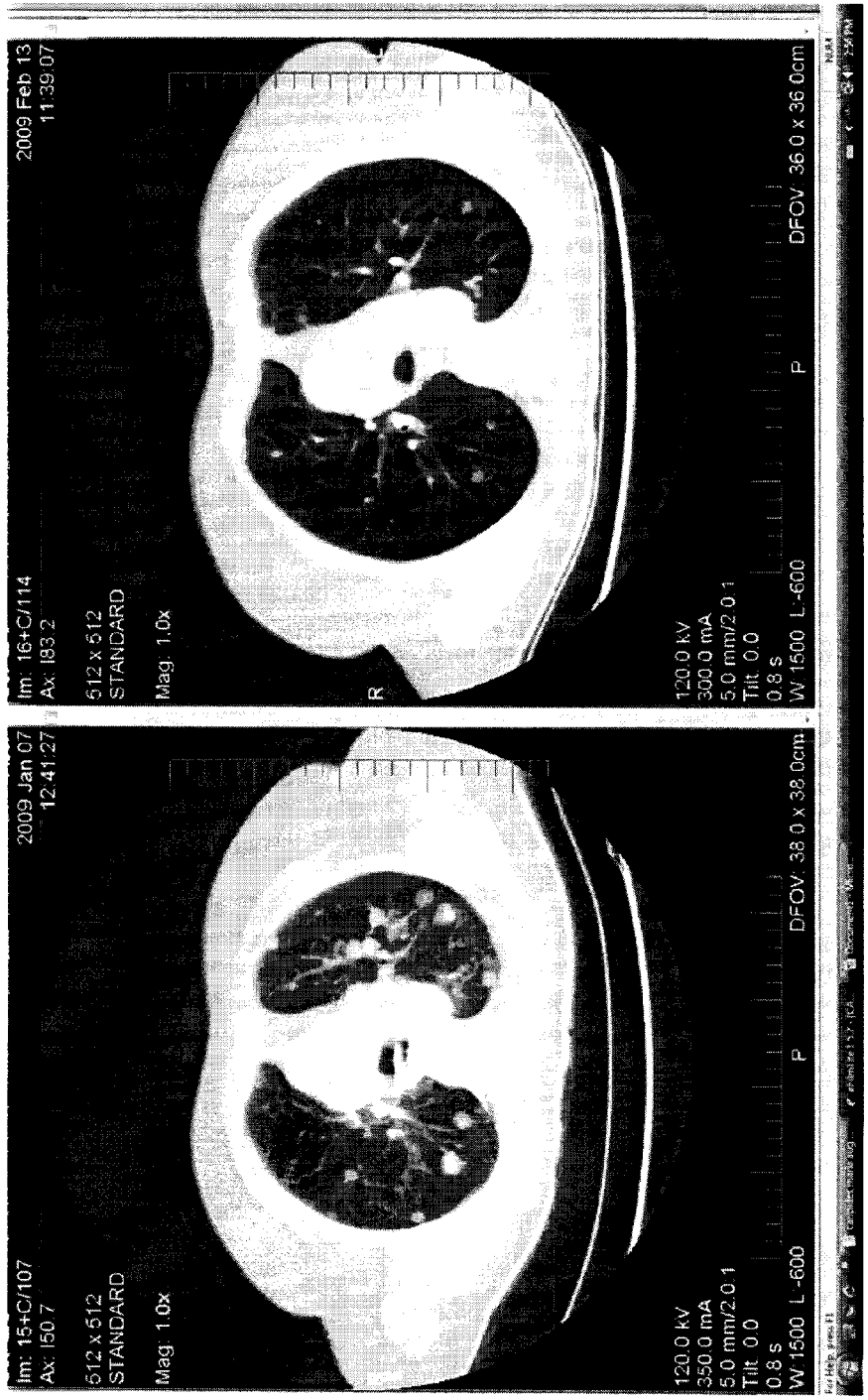
FIGS. 3A-3D are images showing a CT scan of the patient's lung prior to (FIGS. 3A and 3C) and following (FIGS. 3B and 3D) treatment with ANG1005.
Figures 3C, 3D:
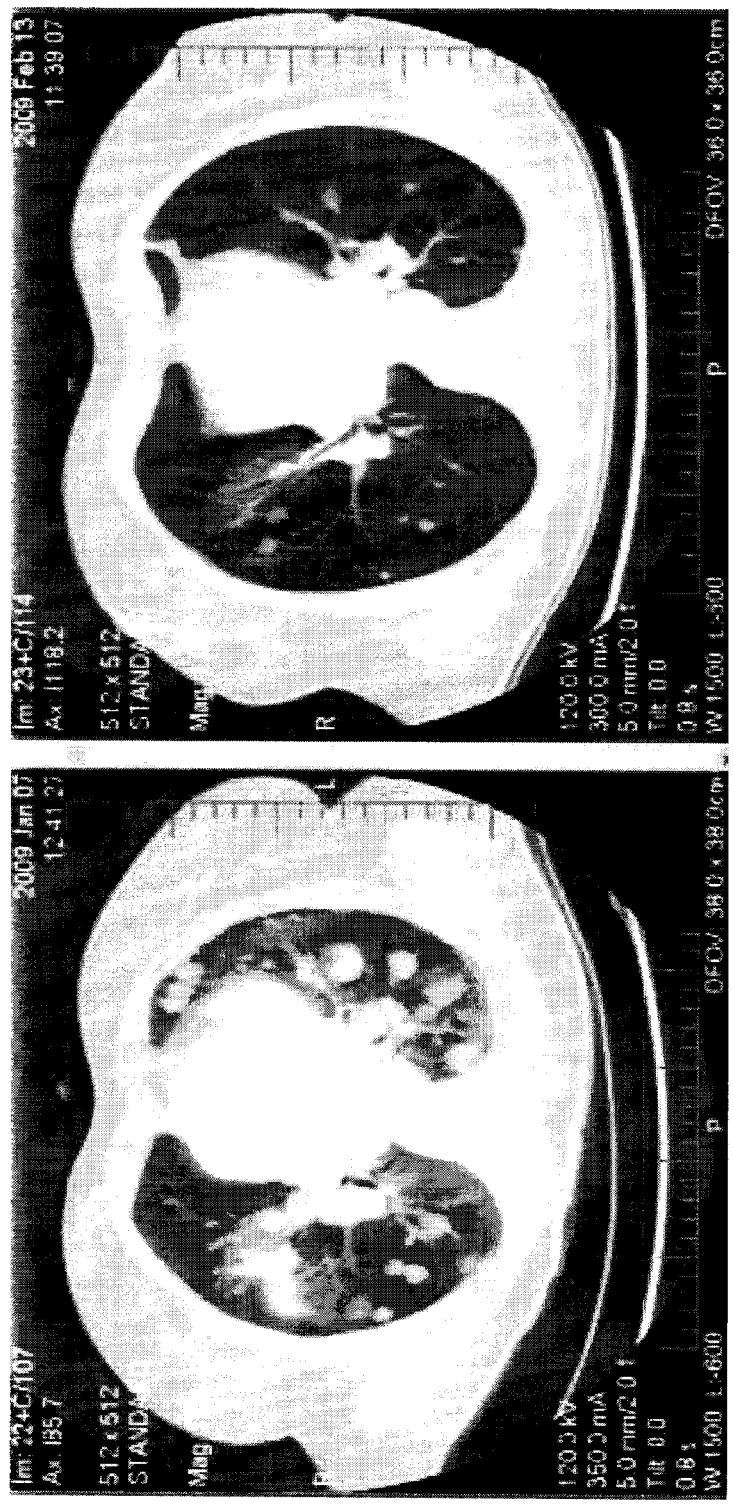
Figures 4A, 4B:
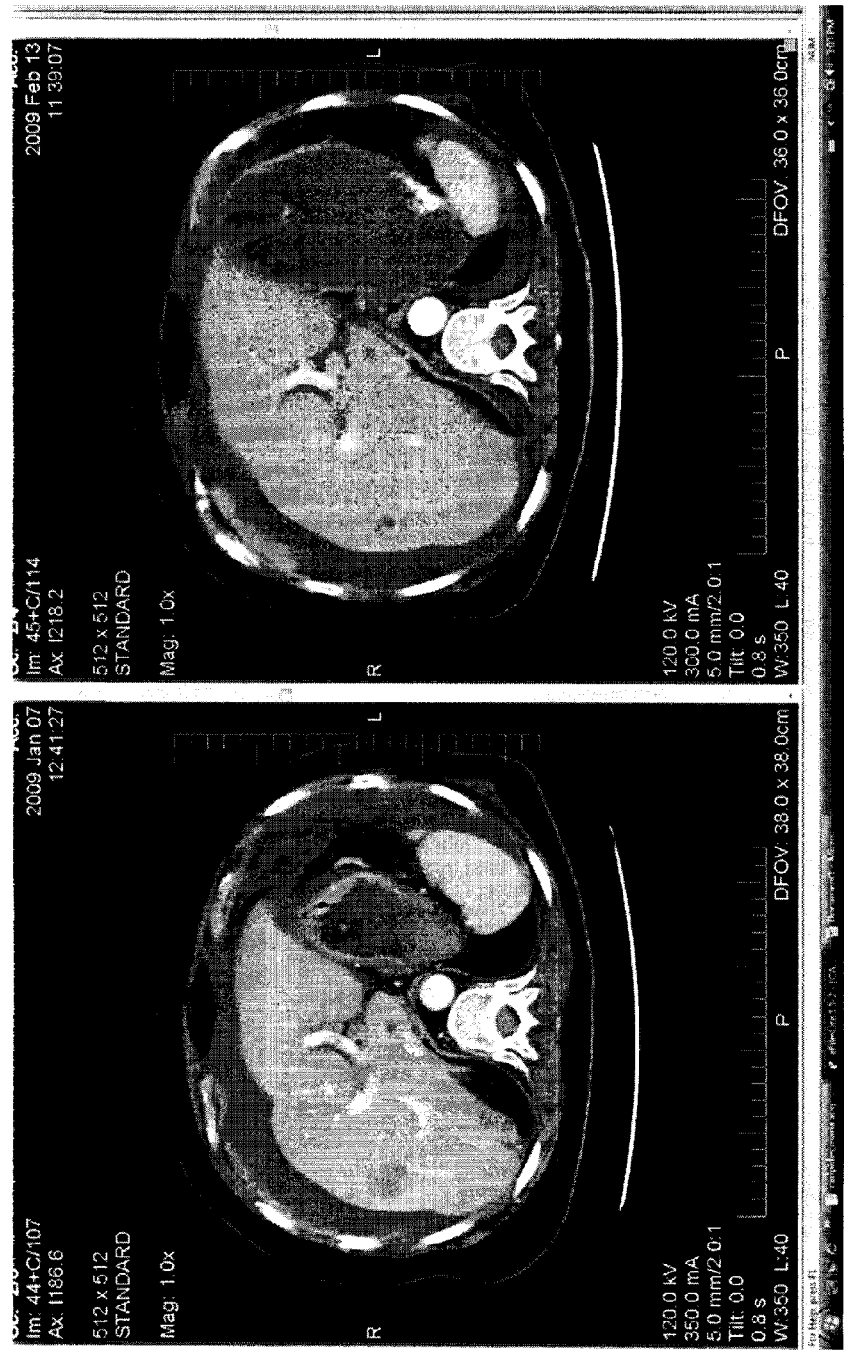
FIGS. 4A and 4B are images showing a CT scan of the patient's abdomen, including liver, prior to (FIG. 4A) and following (FIG. 4B) treatment with ANG1005.
Figures 5A, 5B:
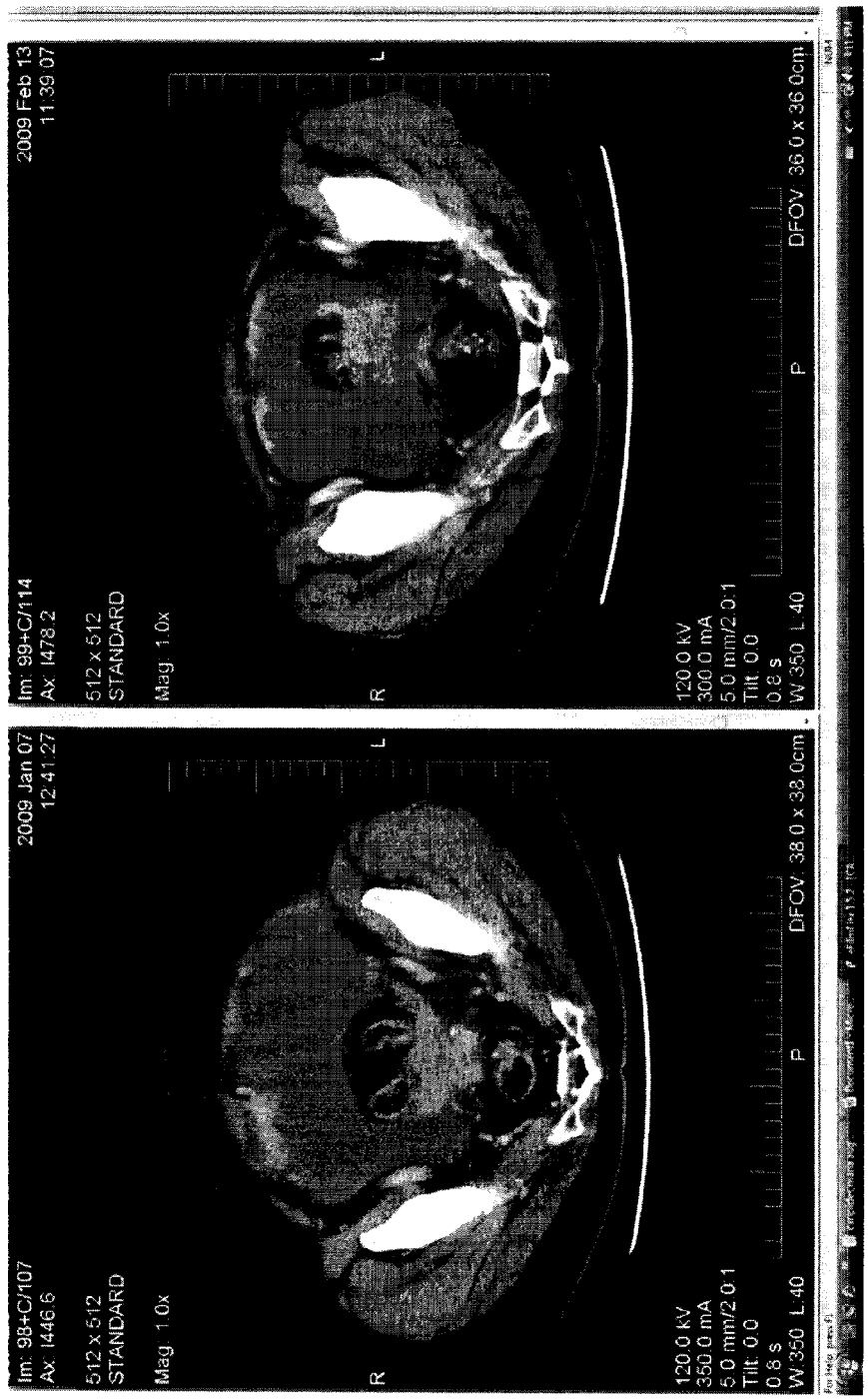
FIGS. 5A and 5B are images showing a CT scan of the patient's pelvis prior to (FIG. 5A) and following (FIG. 5B) treatment with ANG1005.

The patient entered the clinical trial in January 2009. CT scans performed on Jan. 7, 2009, prior to ANG1005 treatment, indicated the presence of metastases in the brain (FIG. 2A), lungs (FIGS. 3A and 3C), and liver (FIG. 4A). Metastases were also detected in the lymph nodes. CT scans of the liver and pelvis were also performed (FIGS. 4A and 5A). On Jan. 8, 2009, the patent was administered a single dose of ANG1005 intravenously. Three weeks later, a second 650 mg/m$^2$ dose was administered. Following these administrations, a surprising reduction in the tumor volume occurred. A CT scan performed Feb. 13, 2009 indicated that a substantial reduction in the size of brain metastases (FIG. 2B) as well as lung metastases (FIGS. 3B and 3D) and liver (FIG. 4B). CT scans of the pelvis (FIG. 5B) are also shown. The patient received the third ANG1005 does on Feb. 19, 2009. Based on these observations, we believe that ANG1005 is surprisingly well suited for treatment of metastatic cancer, particularly where the patient is resistant or is determined to be resistant to standard chemotherapeutic agents.

Clinical Trial Results

The patient described above is a participant in one of two ongoing FDA trials for the ANG1005 therapeutic. The status of the first clinical trial is summarized in Table 1 below. These trials were performed to determine safety of the ANG1005. The first trial involved patients having various brain cancers: anaplastic oligodendroglioma (AO), oligoastrocytoma (OA), anaplastic astrocytoma (AA), and glioblastoma multiforme (GBM).

TABLE 1

| Patient # | Age/Gender | Dx | Dose (mg/m$^2$) | Prior Taxane | # Cycles | Current Status | Overall Tumor Assessment | Comments |
|---|---|---|---|---|---|---|---|---|
| 114 | 44/F | AO | 105 | No | 4 | Withdrawn | PD (12 wks.) | |
| 115 | 43/M | OA Mixed | 105 | No | 4 | Withdrawn | PD (12 wks.) | |
| 117 | 43/M | AO | 105 | No | 2 | Withdrawn | PD (6 wks.) | |
| 118 | 43/F | AA | 105 | No | 2 | Withdrawn | PD (6 wks.) | |
| 119 | 56/M | GBM | 200 | No | 2 | Withdrawn | PD (6 wks.) | |
| 120 | 78/M | GBM | 200 | No | 2 | Withdrawn | PD (6 wks.) | |
| 121 | 41/M | AO | 200 | No | 3 | Withdrawn | SD (6 wks.) | SAE (7 days after Cycle 3): Ataxia and hemorrhage (not related to ANG1005) MRI at 6 weeks shows ↑ 22% |
| 122 | 73/M | GBM | 200 | No | 1 + 1 | Withdrawn | | Surgical sub-study patient (Will continue in core study) |

TABLE 1-continued

| Patient # | Age/Gender | Dx | Dose (mg/m²) | Prior Taxane | # Cycles | Current Status | Overall Tumor Assessment | Comments |
|---|---|---|---|---|---|---|---|---|
| 123 | 59/F | GBM | 300 | No | 4 | Active | SD (6 wks.) | |
| 124 | 69/F | GBM | 300 | No | 2 | Withdrawn | PD (6 wks.) | |
| 125 | 63/F | GBM | 300 | No | 4 | Active | SD (6 wks.) | Pt. experienced Grade 2 Neutropenia (ANC = 1.2) |
| 126 | 42/F | GBM | 300 200 | No | 2 | Withdrawn | | |
| 127 | 30/F | GBM | 300 | No | 2 | Withdrawn | PD (6 wks.) | |
| 128 | 51/M | GBM | 300 | | 3 | Active | SD (6 wks.) | |
| 129 | 57/M | GBM | 300 | | 1 | Active | | Fever & Neutropenia (Gr. 3) |
| 130 | 33/M | AO | 420 | | 2 | Active | | |
| 131 | 49/F | AO | 420 | | 2 | Active | | |
| 132 | 66/F | GBM | 420 | | 1 | Active | | Pt. experienced Grade3 Neutropenia (ANC = 0.65) |

PD (Progressive Disease); SD (Stable Disease)

A second ongoing trial involving patients suffering from metastatic cancer has also begun. Results from this trial are shown in Table 2 below. The ovarian cancer patient described above is represented as patient 134 in Table 2.

TABLE 2

| Patient # | Age/Gender | Dx | Dose (mg/m²) | Prior taxane | # Cycles | Current Status | Overall Tumor assessment | Comments |
|---|---|---|---|---|---|---|---|---|
| 127 | 41/F | NSCLC Mets: Brain | 420 550 420 | Yes | 10 | Active | MR 24 Weeks | Investigator has received approval to increase dose to 550 mg/m² for seventh cycle; 10th cycle decreased to 420 mg/m2 due to peripheral neuropathy |
| 129 | 38/M | Melanoma Mets: Brain | 550 | No | 5 | Withdrawn | SD 12 weeks | Patient admitted to hospital on February 6th for pain (unlikely related to ANG1005). Patient does not wish to continue in study. |
| 131 | 48/F | Colon cancer Mets: Lung, liver | 650 550 | No | 2 | Withdrawn | PD 6 Weeks | C1: febrile neutropenia (DLT) C2: dose delay and reduction to 550 mg/m². Febrile neutropenia reported at D8 |
| 132 | 36/F | NSCLC Mets: bone | 650 | Yes | 1 | Withdrawn | N/E | Patient hospitalized twice (not related to ANG1005). Patient decided to withdraw from study and seek treatment closer to home. Grade 3 neutropenia |
| 133 | 60/F | SCLC Mets: liver, brain | 650 | No | 2 | Withdrawn | N/E | Patient hospitalized with pneumothorax, deceased days after discharge. |

TABLE 2-continued

| Patient # | Age/Gender | Dx | Dose (mg/m$^2$) | Prior taxane | # Cycles | Current Status | Overall Tumor assessment | Comments |
|---|---|---|---|---|---|---|---|---|
| 134 | 73/F | Ovarian cancer Mets: lung, lymph, brain | 650 | Yes | 4 | Withdrawn | PR 6 weeks | Grade 4 neutropenia, treated with G-CSF. Grade 4 neutropenia at Day 8, treated with G-CSF. 80% reduction in primary, also reduction in brain Patient progressed on 2 prior course of taxane Deceased |
| 135 | 60/M | SCLC Mets: brain | 650 550 | No | 4 | Active | PR (6 wks.) PD (12 wks.) | Grade 3 neutropenia at Day 8, Grade 4 at Day 12 (untreated), resolved within 7 days Dose reduced to 550 mg/m2 |
| 136 | 53/M | Melanoma Mets: lung | 650 | No | 3 | Withdrawn | SD | Grade 3 neutropenia at Day 8, grade 2 at Day 15 Infusion reaction at Cycle 2, dosing successfully completed |
| 137 | 66/M | NSCLC Mets: Brain | 700 | | 3 | Active | SD | Grade 3 Neutropenia at Day 21 Grade 4 Neutropenia at cl. 2. |
| 138 | 44/F | Breast Ca. Mets: Brain | 700 650 | | 3 | Active | SD | Cl. 1 Grade 4 Neutropenia |
| 139 | 28/M | Squamous Cell Ca w/Neck, Lung, Bone, Spleen, Pancreas, Left Kidney & Brain Mets | 700 | | | | | Patient deceased |
| 140 | 49/F | Breast Ca w/Liver, Gallbladder, Spinal Cord, & Brain Mets | 700 650 | | 3 | Active | MR | Cl. 1: Grade 4 Neutropenia and Grades 3 and 4 thrombocytopenia |
| 141 | 81/F | SCLC w/Spleen & Brain Mets | 700 650 | | | Active | | Cl. 1: Pt experienced Gr. 4 Neutropenia (ANC = 0.42) & Gr. 2 Platelets (62) |
| 142 | 49/F | Breast Ca w/Lung, Liver, Bone & Brain Mets | 700 | | 1 | Withdrawn | | Headache/ Hypotension/ Acute Renal Failure Deceased |
| 143 | 45/F | Breast Ca w/Lung, Neck, Liver | 650 | | 1 | Active | | |

NSCLC: Non small cell lung cancer
SCLC: Small cell lung cancer
PR (Partial Response); MR (Minor Response); SD (Stable Disease);

Ovarian Cancer

The methods of the invention include treatment of a patient having ovarian cancer. Ovarian cancer starts with formation of a tumor in the ovary of a patient. The ovaries include three different tissues types, epithelial, germ, and stromal, from which a tumor can arise. Most (85-90%) ovarian cancers are derived from epithelial tissue, which are generally ovarian carcinomas or adenocarcinomas. Other ovarian cancers include germ cell tumors and stromal cell tumors.

Risk Factors for Ovarian Cancer

The methods of the invention may involve treatment of patient that has any one or more of risk factors for ovarian cancer. Risk factors for developing ovarian cancer include age, obesity, and family history of ovarian cancer, personal history of breast cancer, high fat diet. Genetic risk factors include mutations on the BRCA1 and BRCA2 genes. Risk for ovarian cancer is reduced in individuals who have been pregnant, have taken oral contraceptives (birth control pills), and have had a tubal ligation.

Ovarian Cancer Stages

The methods of the invention may involve treatment of any stage or grade of ovarian cancer. Ovarian cancer is staged based on three categories: the T, N, and M categories and is further graded based on cellular morphology. The T categories are based on the location of cancer, i.e., whether the cancer is confined to the ovary or ovaries. N is evaluated based on whether the cancer has spread to the lymph nodes, and M is based on whether the cancer has spread to distant organs. These categories are described in detail below.

The T category is divided into three subcategories: T1, where the cancer is confined to one or both ovaries; T2, where the cancer extends from one or both ovaries into pelvic tissues, and T3, where the cancer is in one or both ovaries and has spread to the abdominal lining (peritoneum) outside the pelvis.

Each of T1, T2, and T3 categories are further subdivided. T1 is divided into T1a, T1b, and T1c. In T1a stage cancer, the cancer is only inside one ovary, is not on the outside of the ovary, doesn't penetrate the tissue covering the ovary (the capsule), and is not in fluid taken from the pelvis. In T1b stage cancer, the cancer is inside both ovaries, but otherwise has the features of T1a stage cancer. In T1c stage cancer, the cancer is in one or both ovaries and is either on the outside of an ovary, has grown through the capsule of an ovary, or is in fluid taken from the pelvis.

T2 is likewise divided into the subcategories T2a, T2b, and T2c. In T2a stage cancer, the cancer has metastasized to the uterus or to the fallopian tubes, but cancer cells are not found in fluid taken from the pelvis. In T2b stage cancer, the cancer has spread to pelvic tissues other than the uterus and fallopian tubes, but it is not in fluid taken from the pelvis. In T2c stage cancer, the cancer has spread to the uterus, fallopian tubes, and/or other pelvic tissues and is also in fluid taken from the pelvis.

T3 is also divided into three subcategories: T3a, T3b, and T3c. In T3a stage cancer, the metastases can only be seen under a microscope. In T3b stage cancer, the metastases are visible, but no tumor is bigger than 2 cm. In T3c stage cancer, the metastases are larger than 2 cm.

The N categorization is based on whether the cancer has spread to regional lymph nodes. The cancer is graded N0 if there is no lymph node involvement and is graded N1 if cancer cells are found in the lymph nodes close to the ovarian tumor.

The M categorization is based on whether the cancer has spread to distant organs, such as the liver, lungs, or non-regional lymph nodes. If there is no distant spread, the cancer is graded M0. If the cancer has spread to distant organs, including the inside of the liver and the lungs, it is graded M1.

Finally the cancer is graded based on its morphology, where a higher grade indicates a greater likelihood of metastasizing. Grade 1 indicates a well-differentiated tumor that appears similar to normal ovarian tissue. Grade 2 indicates a tumor that is not as well differentiated; it looks less like ovarian tissue than a Grade 1 tumor. A Grade 3 tumor is characterized as being poorly differentiated and does not look like ovarian tissue.

Once a patient's T, N, and M scores have been determined, this information is combined in a process called stage grouping to determine the stage, expressed in Roman numerals from stage I (least advanced) to stage IV (most advanced). The following Table sets forth the various stages of ovarian cancer.

TABLE 3

| Stage | Sub-stage | T, N, M | Description |
|---|---|---|---|
| I | IA | T1a, N0, M0 | Cancer in one ovary, confined to the inside of the ovary with no cancer on the outer surface of the ovary. No cancer cells found in washings from the abdomen and pelvis. |
|  | IB | T1b, N0, M0 | Same as IA, with cancer in both ovaries |
|  | IC | T1c, N0, M0 | IA or IB, with one or more of the following: cancer on the outer surface of at least one ovary; in the case of cystic tumors, the capsule has ruptured; cancer cells found in fluid or washings from the abdomen. |
| II | IIA | T2a, N0, M0 | Cancer has spread to or has invaded the uterus, fallopian tubes, or both. Cancer cells not found in the abdomen. |
|  | IIB | T2b, N0, M0 | Cancer has spread to pelvic organs such as the bladder, sigmoid colon, or rectum. Cancer cells not found in the abdomen. |
|  | IIC | T2c, N0, M0 | IIA or IIB, with cancer cells found in the abdomen |
| III | IIIA | T3a, N0, M0 | Biopsies show deposits of cancer in the lining of the upper abdomen under microscope. Cancer has not spread to lymph nodes. |
|  | IIIB | T3b, N0, M0 | Deposits of cancer in the abdomen are large enough to see, but smaller than 2 cm across. Cancer has not spread to the lymph nodes. |
|  | IIIC | Any T, N1, M0 and/or T3c, N0, M0 | Cancer is in one or both ovaries. Cancer either has spread to lymph nodes (any T, N1, M0) or is visible in deposits larger than 2 cm across in the abdomen (T3c, N0, M0). |
| IV | n/a | Any T, Any N, M1 | Cancer has spread outside the abdomen |

Standard Therapy for Ovarian Cancer

The methods of the invention may include, in addition to administration of a conjugates described herein, treatment using standard, art-recognized therapeutic options for a patient having ovarian cancer. The standard therapy or therapies will depend on the stage of cancer. The methods of the invention may also include administering a conjugate following prior treatment with one or more of the standard ovarian cancer therapies (e.g., following failure of the standard therapy).

In well-differentiated or moderately differentiated non-metastatic cancer (e.g., Grade 1 or 2), surgical removal of the tumor and surrounding tissue (e.g., bilateral salpingo-oophorectomy with omentectomy) is often sufficient for treatment of Stage IA or IB disease. If the tumor is Grade 3, densely adherent, or Stage IC, the treatment may further include intraperitoneal P-32 or radiation therapy or systemic chemotherapy based on platinums (e.g., carboplatin or cisplatin) alone or in combination with an alkylating agent. Other first line therapies include systemic chemotherapy based on platinums (e.g., carboplatin or cisplatin) with paclitaxel or administration of a nitrogen mustard (e.g., cyclophosphamide, mechlorethamine (mustine), uramustine (uracil mustard), melphalan, chlorambucil, and ifosfamide), nitrosoureas (e.g., carmustine and streptozocin), alkyl sulfonates (e.g., busulfan), or doxorubicin.

If the first line therapy fails, topotecan and hexamethylamine are FDA-approved as second line therapies. Other drugs used in second line therapy include doxorubicin, Doxil® (doxorubicin HCl liposome injection), Hexalen® (altretamine; hexamethylmelamine, Ifex® (ifosfamide), VePesid® (etoposide (VP-16)), 5-FU (5-fluorouracil), gemcitabine, and vinorelbine. These drugs can be administered alone or in combination with each other, with first line agents, or with other anticancer therapeutics (e.g., those described herein).

Treatment of Drug Resistant Cancer

The patient being treated in a method of the present invention may have a cancer that is drug resistant. Because the conjugates of the invention have activity even in cancers that have demonstrated resistance to standard chemotherapeutic agents, the methods of the invention are particularly useful in treating such drug resistant cancers.

Drug resistance typically arises following treatment with a particular chemotherapeutic. Multiple drug resistance (MDR) can arise when a cell overproduces the p-glycoprotein (P-gp) efflux transporter. As many chemotherapeutic drugs can be P-gp substrates, including vinblastine, doxorubicin, etoposide, colchicine, and paclitaxel, overexpression of P-gp in a cancer cell can lead to broad spectrum of resistance toward chemotherapeutic agents.

We have previously shown that paclitaxel conjugated to Angiopep-1 or Angiopep-2 are not P-gp substrates and thus should not be sensitive to P-gp overexpression in tumor cells; see, e.g., pages 46-47 and FIG. 9A of International Application Publication WO 2007/009229. Thus, the drug conjugates described herein are useful in treating patients having cancer that is resistant to standard chemotherapeutic drugs.

Enhanced Uptake into LRP Expressing Cells

Figure 6A:
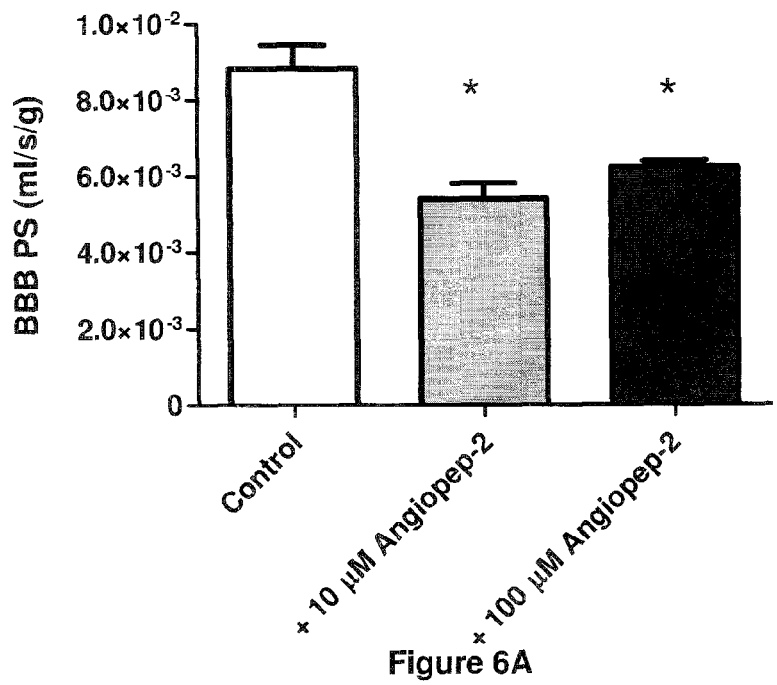
FIGS. 6A and 6B are graphs showing inhibition of ANG1005 by the Angiopep-2 peptide (FIG. 6A) or by receptor associated protein (RAP) or aprotinin (FIG. 6B).
Figure 6B:
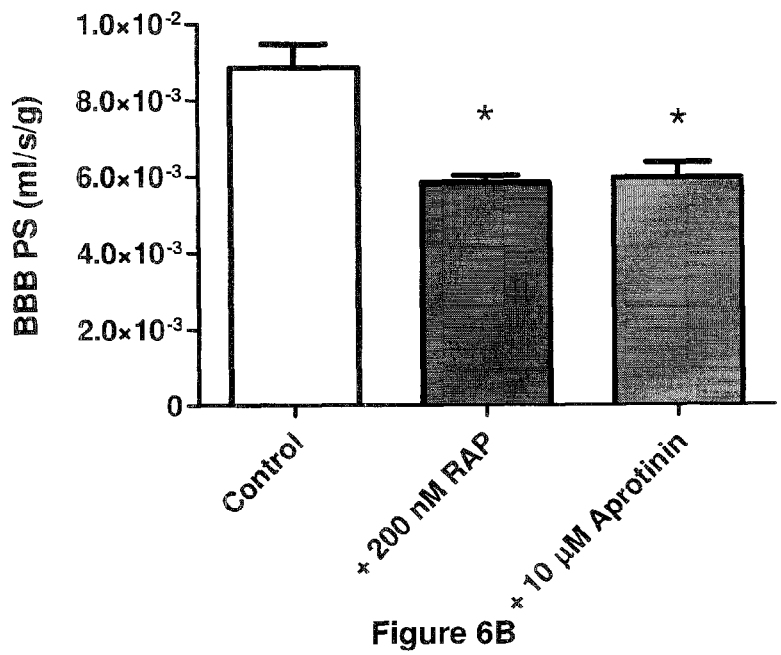

The methods of the invention may be especially useful in treating cancers having cells that express low density lipoprotein-related protein (LRP) receptor. The LRP receptor is expressed on the surface of cells, and is capable of binding to various substrates including aprotinin, β-amyloid, tissue plasminogen activator (tPA), melano-transferrin, and receptor associated peptide (RAP). The peptides described herein were designed based on the consensus kunitz-domain sequences that act as LRP receptor ligands (see, e.g., PCT Publication No. WO 2004/060403). Uptake of the conjugates including Angiopep-1 or Angiopep-2 is inhibited by LRP ligands, thus indicating involvement of LRP in this process. Specifically, the LRP ligands RAP (200 nM) and aprotinin (10 μM) are capable of reducing brain uptake of an Angiopep conjugate. Angiopep-2 (10 or 100 μM) is similarly able to reduce uptake of the conjugates into cells (FIGS. 6A and 6B).

Figure 7:
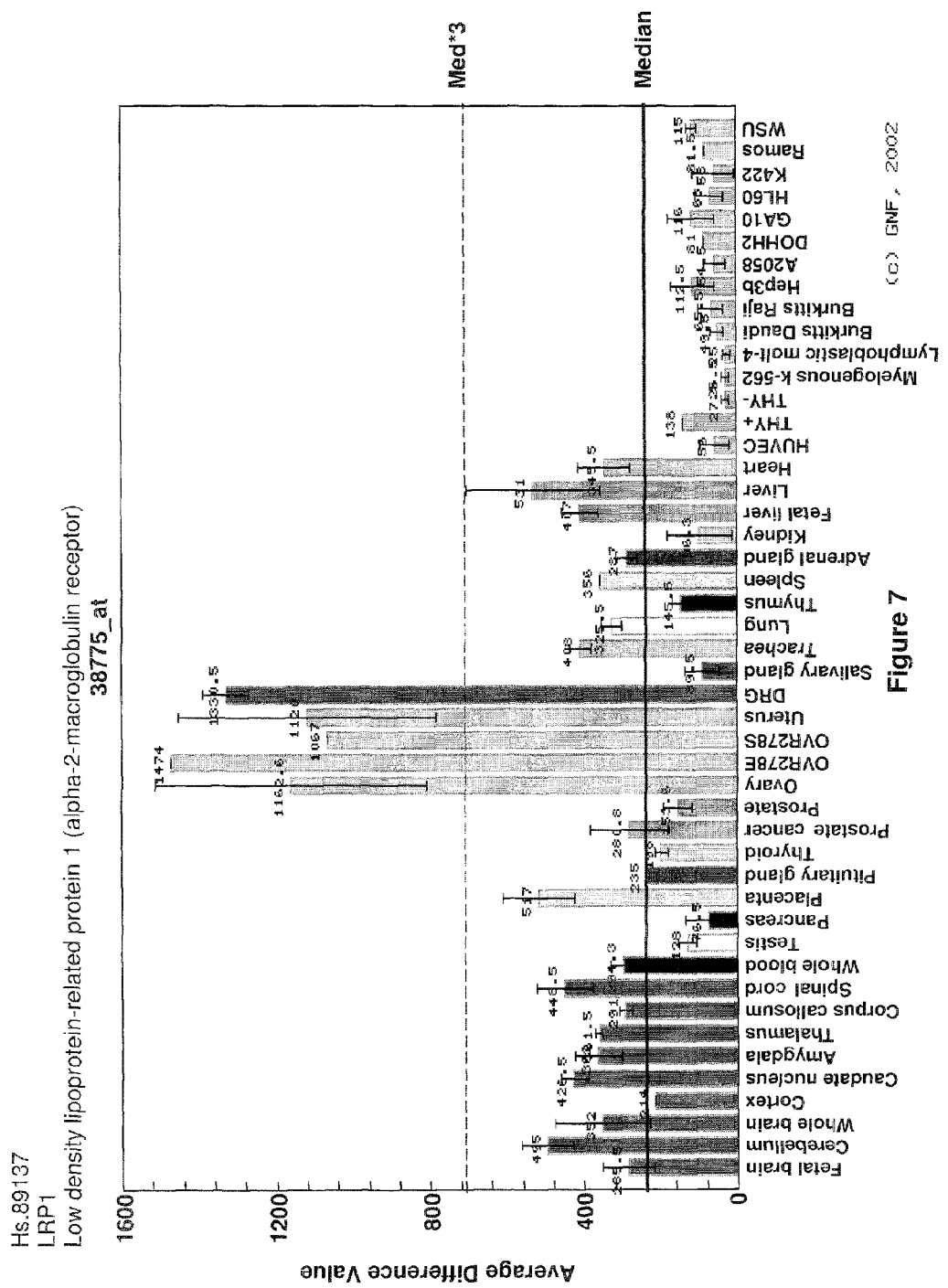
FIG. 7 is a graph showing LRP expression in various cell types and cell lines. Data is taken from the Gene Expression Atlas from the Genetics Institute of the Novartis Research Foundation (available online at http://expression.gnf.org/cgi-bin/index.cgi#Q).

Ovarian cells express high levels of LRP (FIG. 7). Accordingly, cancers originating from ovarian cells are well suited for treatment using therapeutics that target LRP-expressing cells.

The results described in FIGS. 4A and 4B were obtained using an in situ rat brain perfusion. Male Sprague Dawley rats were anesthetized with 40 m/kg i.p., of sodium pentobarbital (Nembutal, Abbott Laboratories, North Chicago, Ill., USA). The neck region was shaved and the common carotid artery was exposed. The external carotid artery was ligated, but the pterygopalatine artery was not occluded. A PE-60 catheter filled with heparinized 0.9% saline (100 IU/mL) was inserted into the common carotid artery upon ligation. A heating pad linked to YSI feedback controller device (Yellow Springs Instruments, Yellow Springs, Ohio, USA) was used to maintain the rat body temperature at 37° C. The PE-60 catheter was attached to a glass syringe filled with the tracer; with or without inhibitors, in a bicarbonate-buffered physiological saline (Smith Q R., Pharm Biotechnol 8:285-307, 1996) mounted on a Harvard infusion pump (Harvard Biosciences, South Natick, Mass., USA) maintained at 37° C. Dual-labeled experiments were performed for studying the brain uptake. [$^{14}$C]Sucrose was used as a vascular volume marker. Perfusion was started upon severing the heart to stop blood flow to the brain. The fluid was perfused into the common carotid artery at a rate of 5 ml/min for a period of 15-300 sec. At the end of perfusion, the rat was decapitated and the brain was harvested. The left hemisphere of the brain was dissected into regions as described previously (Takasato et al., Am J Physiol 247:H484-93, 1984). The samples were weighed and counted using the gamma counter (Cobra 600) to determine the $^{125}$I labeled drug. In the inhibition studies, the LRP ligands or Angiopep peptides were co-perfused at the indicated concentrations.

Combination Therapy

The methods of the invention may include administration of second therapeutic agent or treatment with a second therapy (e.g., a therapeutic agent or therapy that is standard in the art). Exemplary therapeutic agents include abarelix, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin (e.g., sodium), darbepoetin alfa, dasatinib, daunorubicin, daunomycin, decitabine, denileukin, denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, mechlorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa-2b, pemetrexed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., HCl), toremifene, Tositumomab/I-131 (tositumomab), trastuzumab, trastuzumab, tretinoin (ATRA), uracil mustard, valrubicin, vinblastine, vincristine, vinorelbine, vorinostat, zoledronate, and zoledronic acid. Exemplary derivatives of paclitaxel are described in U.S. Pat. No. 6,911,549, the entire contents of which are hereby incorporated by reference.

Other agents include that can be used include antiestrogen agents such as tamoxifen (e.g., citrate), raloxifene, toremifene, and SCH 57068.

Polypeptide Conjugates

The methods of the invention include administration of a peptide-anticancer agent conjugate, such as those described in U.S. Patent Applications Publication Nos. 2006/0182684, and 2006/0189515, and U.S. Provisional Application No. 61/008,880, filed Dec. 20, 2007. Such conjugates may include any polypeptide described herein, an agent capable of treating ovarian cancer such as paclitaxel or a paclitaxel analog (e.g., those described herein), and a linker (e.g., those described herein). Paclitaxel conjugates are exemplified by ANG1005, which includes the AngioPep-2 peptide (SEQ ID NO:97) conjugated to three paclitaxel molecules through ester linkages at the N-terminus, and through lysines at positions 10 and 15.

The conjugates, in certain embodiments, can cross the blood-brain barrier (BBB) or can be preferentially targeted to certain cell types, such as ovary, liver, lung, kidney, muscle cells or may be targeted to tumor cells (of any cell type described herein). These agents conjugated to these peptides can exhibit increased uptake into the targeted cells, for example, by receptor-mediated endocytosis (e.g., through an LRP receptor). The conjugated agents may, either alternatively or in addition, exhibit increased stability or reduced expulsion from the cell (e.g., due to P-glycoprotein mediated efflux). Conjugates may further have activity in cancer cells that are resistant to standard chemotherapies.

Polypeptides

The methods of the invention can include administration a conjugate include any polypeptide described herein, for example, any of the polypeptides described in Table 4 (e.g., a polypeptide defined in any of SEQ ID NOS:1-105 and 107-116 such as SEQ ID NOS:1-97, 99, 100, 101, or 107-116), or any fragment, analog, derivative, or variant thereof. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. Other modifications are described in greater detail below.

The conjugates can also feature fragments of these polypeptides (e.g., a functional fragment). In certain embodiments, the fragments are capable of entering or accumulating in a particular cell type (e.g., ovary, liver, lung, kidney, spleen, or muscle) or capable of crossing the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

Additional polypeptides may be identified by using one of the assays or methods described in U.S. Patent Application Publication No. 2006/0189515, which is hereby incorporated by reference, or by any method known in the art. For example, a candidate vector may be produced by conventional polypeptide synthesis, conjugated with Taxol and administered to a laboratory animal. A biologically active vector may be identified, for example, based on its efficacy to increase survival of an animal injected with tumor cells and treated with the conjugate as compared to a control which has not been treated with a conjugate (e.g., treated with the unconjugated agent).

In another example, a biologically active polypeptide may be identified based on its location in the parenchyma in an in situ cerebral perfusion assay. In vitro BBB assays, such as the model developed by CELLIAL™ Technologies, may be used to identify such vectors.

Assays to determine accumulation in other tissues may be performed as well. Labeled conjugates of a polypeptide can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide can be labeled with a radioactive isotope (e.g., $^{125}$I). The polypeptide is then administered to an animal. After a period of time, the animal is sacrificed, and the animal's organs are extracted. The amount of radioisotope in each organ can then be measured using any means known in the art. By comparing the amount of a labeled candidate polypeptide in a particular organ without amount of labeled control, the ability of the candidate polypeptide the rate or amount of accumulation of a candidate polypeptide in a particular tissue can be ascertained. Appropriate negative controls include any polypeptide known not be transported into a particular cell type.

TABLE 4

| SEQ ID NO: | | | | | | | | | | | | | | | |
|---|---|---|---|---|---|---|---|---|---|---|---|---|---|---|---|
| 1 | T | F | V | Y | G | G | C | R | A | K | R | N | N | F | K | S | A | E | D |
| 2 | T | F | Q | Y | G | G | C | M | G | N | G | N | N | F | V | T | E | K | E |
| 3 | P | F | F | Y | G | G | C | G | G | N | R | N | N | F | D | T | E | E | Y |
| 4 | S | F | Y | Y | G | G | C | L | G | N | K | N | N | Y | L | R | E | E | E |
| 5 | T | F | F | Y | G | G | C | R | A | K | R | N | N | F | K | R | A | K | Y |
| 6 | T | F | F | Y | G | G | C | R | G | K | R | N | N | F | K | R | A | K | Y |
| 7 | T | F | F | Y | G | G | C | R | A | K | K | N | N | Y | K | R | A | K | Y |
| 8 | T | F | F | Y | G | G | C | R | G | K | K | N | N | F | K | R | A | K | Y |
| 9 | T | F | Q | Y | G | G | C | R | A | K | R | N | N | F | K | R | A | K | Y |
| 10 | T | F | Q | Y | G | G | C | R | G | K | K | N | N | F | K | R | A | K | Y |
| 11 | T | F | F | Y | G | G | C | L | G | K | R | N | N | F | K | R | A | K | Y |
| 12 | T | F | F | Y | G | G | S | L | G | K | R | N | N | F | K | R | A | K | Y |
| 13 | P | F | F | Y | G | G | C | G | G | K | K | N | N | F | K | R | A | K | Y |
| 14 | T | F | F | Y | G | G | C | R | G | K | G | N | N | Y | K | R | A | K | Y |
| 15 | P | F | F | Y | G | G | C | R | G | K | R | N | N | F | L | R | A | K | Y |
| 16 | T | F | F | Y | G | G | C | R | G | K | R | N | N | F | K | R | E | K | Y |
| 17 | P | F | F | Y | G | G | C | R | A | K | K | N | N | F | K | R | A | K | E |
| 18 | T | F | F | Y | G | G | C | R | G | K | R | N | N | F | K | R | A | K | D |
| 19 | T | F | F | Y | G | G | C | R | A | K | R | N | N | F | D | R | A | K | Y |
| 20 | T | F | F | Y | G | G | C | R | G | K | K | N | N | F | K | R | A | E | Y |
| 21 | P | F | F | Y | G | G | C | G | A | N | R | N | N | F | K | R | A | K | Y |

TABLE 4-continued

| SEQ ID NO: | Sequence |
|---|---|
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G K R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R F |
| 96 | R Q I K I W F Q N R R M K W K K |
| 97 | T F F Y G G S R G K R N N F K T E E Y |

TABLE 4-continued

| SEQ ID NO: | |
|---|---|
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | T F F Y G G S R G K R N N F R T E E Y |
| 112 | T F F Y G G S R G R R N N F R T E E Y |
| 113 | C T F F Y G G S R G K R N N F K T E E Y |
| 114 | T F F Y G G S R G K R N N F K T E E Y C |
| 115 | C T F F Y G G S R G R R N N F R I E E Y |
| 116 | T F F Y G G S R G R R N N F R T E E Y C |

Figure 1:
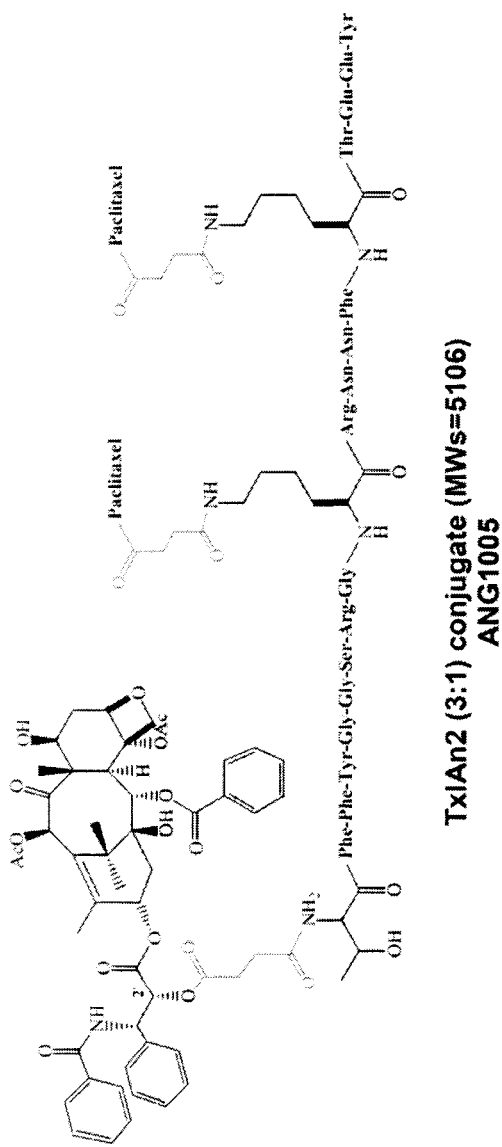
FIG. 1 is a schematic diagram of the ANG1005 structure. ANG1005 includes three molecules of paclitaxel conjugated to the Angiopep-2 peptide (SEQ ID NO:97).

Peptide no. 5 includes the sequence of SEQ ID NO: 5 and is amidated at its C-terminus (see for example FIG. 1)
Peptide No. 67 includes the sequence of SEQ ID NO: 67 and is amidated at its C-terminus (see for example FIG. 1)
Peptide No. 76 includes the sequence of SEQ ID NO: 76 and is amidated at its C-terminus (see for example FIG. 1).
Peptide no. 91 includes the sequence of SEQ ID NO: 91 and is amidated at its C-terminus (see for example FIG. 1).
Peptide No. 107 includes the sequence of SEQ ID NO: 97 and is acetylated at its N-terminus.
Peptide No. 109 includes the sequence of SEQ ID NO: 109 and is acetylated at its N-terminus.
Peptide No. 110 includes the sequence of SEQ ID NO: 110 and is acetylated at its N-terminus.

The amine groups of Angiopep-1 (SEQ ID NO:67) and Angiopep-2 (SEQ ID NO:97) have been used as sites for conjugation of agents. To study the role of amine groups in conjugation and their impact in the overall transport capacity of these vectors, new vectors, based on the Angiopep-1 and Angiopep-2 sequence, were designed with variable reactive amine groups and variable overall charge. These polypeptides are shown in Table 5.

TABLE 5

Vectors with variable amine group targets

| Polypeptide Name | Polypeptide Sequences | Reactive amines (positions) | Charge | SEQ ID No. |
|---|---|---|---|---|
| Angiopep-3* | Ac[1]-TFFYGGSRGKRNNFKTEEY | 2 (10, 15) | +1 | 107 |
| Angiopep-4b | RFFYGGSRGKRNNFKTEEY | 3 (1, 10, 15) | +3 | 108 |
| Angiopep-4a | Ac[1]-RFFYGGSRGKRNNFKTEEY | 2 (10, 15) | +2 | 109 |
| Angiopep-5 | Ac[1]-RFFYGGSRGKRNNFRTEEY | 1 (10) | +2 | 110 |
| Angiopep-6 | TFFYGGSRGKRNNFRTEEY | 2 (1, 10) | +2 | 111 |
| Angiopep-7 | TFFYGGSRGRRNNFRTEEY | 1 (1) | +2 | 112 |

*Angiopep-3 is an acetylated form of Angiopep-2.
[1]Ac represents acetylation.

Modified Polypeptides

The methods of the invention may also include administration of a conjugate that includes a polypeptide with a modification to an amino acid sequence described herein (e.g., polypeptide having a sequence described in any one of SEQ ID NOS:1-105 and 107-112 such as AngioPep-3, -4a, -4b, -5, -6, or -7). In certain embodiments, the modification does not destroy significantly a desired biological activity. In some embodiments, the modification may cause a reduction in biological activity (e.g., by at least 5%, 10%, 20%, 25%, 35%, 50%, 60%, 70%, 75%, 80%, 90%, or 95%). In other embodiments, the modification has no effect on the biological activity or may increase (e.g., by at least 5%, 10%, 25%, 50%, 100%, 200%, 500%, or 1000%) the biological activity of the original polypeptide. The modified polypeptide may have or may optimize one or more of the characteristics of a polypeptide of the invention which, in some instance might be needed or desirable. Such characteristics include in vivo stability, bioavailability, toxicity, immunological activity, or immunological identity.

Polypeptides used in the invention may include amino acids or sequences modified either by natural processes, such as posttranslational processing, or by chemical modification techniques known in the art. Modifications may occur anywhere in a polypeptide including the polypeptide backbone, the amino acid side-chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide may further include an amino acid insertion, deletion, or substitution, either conservative or non-conservative (e.g., D-amino acids, desamino acids) in the polypeptide sequence (e.g., where such changes do not substantially alter the biological activity of the polypeptide).

Substitutions may be conservative (i.e., wherein a residue is replaced by another of the same general type or group) or non-conservative (i.e., wherein a residue is replaced by an amino acid of another type). In addition, a non-naturally occurring amino acid may substituted for a naturally occurring amino acid (i.e., non-naturally occurring conservative amino acid substitution or a non-naturally occurring non-conservative amino acid substitution).

Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogues may be generated by substitutional mutagenesis and retain the biological activity of the original polypeptide. Examples of substitutions identified as "conservative substitutions" are shown in Table 3. If such substitutions result in a change not desired, then other type of substitutions, denominated "exemplary substitutions" in Table 6, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe), (2) neutral hydrophilic: Cysteine (Cys), Serine (Ser), Threonine (Thr)

(3) acidic/negatively charged: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro);

(6) aromatic: Tryptophan (Trp), Tyrosine (Tyr), Phenylalanine (Phe), Histidine (His), (7) polar: Ser, Thr, Asn, Gln
(8) basic positively charged: Arg, Lys, His, and;
(9) charged: Asp, Glu, Arg, Lys, His Other conservative amino acid substitutions are listed in Table 3.

TABLE 6

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Additional Analogues

The conjugates used in the invention may include any polypeptide analog of aprotinin known in the art. For example, U.S. Pat. No. 5,807,980 describes Bovine Pancreatic Trypsin Inhibitor (aprotinin)-derived inhibitors as well as a method for their preparation and therapeutic use, including the polypeptide of SEQ ID NO:102. These polypeptides have been used for the treatment of a condition characterized by an abnormal appearance or amount of tissue factor and/or factor VIIIa such as abnormal thrombosis. U.S. Pat. No. 5,780,265 describes serine protease inhibitors capable of inhibiting plasma kallikrein, including SEQ ID NO:103. U.S. Pat. No. 5,118,668 describes Bovine Pancreatic Trypsin Inhibitor variants, including SEQ ID NO:105. The aprotinin amino acid sequence (SEQ ID NO:98), the Angiopep-1 amino acid sequence (SEQ ID NO:67), and SEQ ID NO:104, as well as some sequences of biologically active analogs may be found in International Application Publication No. WO 2004/060403.

An exemplary nucleotide sequence encoding an aprotinin analogue is illustrated in SEQ ID NO:106 (atgagaccag atttctgcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggtgcttag; Genbank accession No. X04666). This sequence encodes a lysine at position 16 instead of a valine, as found in SEQ ID NO:98. A mutation in the nucleotide sequence of SEQ ID NO:106 may be introduced by methods known in the art to change the produce the polypeptide of SEQ ID NO:98 having a valine in position 16. Additional mutations or fragments may be obtained using any technique known in the art.

Other examples of aprotinin analogs may be found by performing a protein BLAST (Genebank: www.ncbi.nlm.nih.gov/BLAST/) using the synthetic aprotinin sequence (or portion thereof) disclosed in International Application No. PCT/CA2004/000011. Exemplary aprotinin analogs are found under accession Nos. CAA37967 (GI:58005) and 1405218C (GI:3604747).

Conjugates

The polypeptides described herein or derivatives thereof are conjugated to an anticancer agent (e.g., any known in the art). Each polypeptide may be conjugated to at least 1, 2, 3, 4, 5, 6, or 7 agents. In other embodiments, each agent has at least 1, 2, 3, 4, 5, 6, 7, 10, 15, 20, or more polypeptides attached thereto. The conjugates of the invention may be able to promote accumulation (e.g., due to increased uptake or reduced removal) of the agent in a particular cell type or tissue such as ovary, liver, lung, kidney, spleen or muscle of a subject.

The agent may be releasable from the vector after transport into a particular cell type or across the BBB. The agent can be released, for example, by enzymatic cleavage or other breakage of a chemical bond between the vector and the agent. The released agent may then function in its intended capacity in the absence of the vector.

In particular embodiments, the agent is paclitaxel or a paclitaxel analog (e.g., those described herein). Other anticancer agents include abarelix, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin (e.g., sodium), darbepoetin alfa, dasatinib, daunorubicin, daunomycin, decitabine, denileukin, Denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa-2b, pemetrexed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., hcl), toremifene, Tositumomab/I-131 (tositumomab), trastuzumab, trastuzumab, tretinoin (ATRA), uracil mustard, valrubicin, vinblastine, vincristine, vinorelbine, vorinostat, zoledronate, and zoledronic acid.

Other anticancer agents include antibodies. Conjugation of such antibodies may be accomplished using any means known in the art (e.g., using the conjugation strategies described herein). Any diagnostic or therapeutic antibody may be conjugated to one or more (e.g., 2, 3, 4, 5, 6, 7, 8, 9, 10, or more) vectors of the invention. In addition, antibody fragments (e.g., capable of binding to an antigen) may also be conjugated to the vectors of the invention. Antibody fragments include the Fab and Fc regions, heavy chain, and light chain of an antibody (e.g., of any antibody described herein). Exemplary antibodies for use in diagnosis and therapy of cancer include ABX-EGF (Panitimumab), OvaRex (Oregovemab), Theragyn (pemtumomabytrrium-90), Therex, Bivatuzumab, Panorex (Edrecolomab), ReoPro (Abciximab), Bexxar (Tositumomab), MAb, idiotypic 105AD7, Anti-EpCAM (Catumaxomab), MAb lung cancer (from Cytoclonal), Herceptin (Trastuzumab), Rituxan (Rituximab), Avastin (Bevacizumab), AMD Fab (Ranibizumab), E-26 ($2^{nd}$ gen. IgE) (Omalizumab), Zevalin (Rituxan+yttrium-90) (Ibritumomab tiuxetan), Cetuximab, BEC2 (Mitumomab), IMC-1C11, nuC242-DM1, LymphoCide (Epratuzumab), LymphoCide Y-90, CEA-Cide (Labetuzumab), CEA-Cide Y-90, CEA-Scan (Tc-99m-labeled arcitumomab), LeukoScan (Tc-99m-labeled sulesomab), LymphoScan (Tc-99m-labeled bectumomab), AFP-Scan (Tc-99m-labeled), HumaRAD-HN (+yttrium-90), HumaSPECT (Votumumab), MDX-101 (CTLA-4), MDX-210 (her-2 overexpression), MDX-210/MAK, Vitaxin, MAb 425, IS-IL-2, Campath (alemtuzumab), CD20 streptavidin, Avidicin, (albumin+NRLU13), Oncolym (+iodine-131) Cotara (+iodine-131), C215 (+staphylococcal enterotoxin, MAb lung/kidney cancer (from Pharmacia Corp.), nacolomab tafenatox (C242 staphylococcal enterotoxin), Nuvion (Visilizumab), SMART M195, SMART 1D10, CEAVac, TriGem, TriAb, NovoMAb-G2 radiolabeled, Monopharm C, GlioMAb-H (+gelonin toxin), Rituxan (Rituximab), and ING-1. Additional therapeutic antibodies include 5G1.1 (Ecluizumab), 5G1.1-SC (Pexelizumab), ABX-CBL (Gavilimomab), ABX-IL8, Antegren (Natalizumab), Anti-CD11a (Efalizumab), Anti-CD18 (from Genetech), Anti-LFA1, Antova, BTI-322, CDP571, CDP850, Corsevin M, D2E7 (Adalimumab), Humira (Adalimumab), Hu23F2G (Rovelizumab), IC14, IDEC-114, IDEC-131, IDEC-151, IDEC-152, Infliximab (Remicade), LDP-01, LDP-02, MAK-195F (Afelimomab), MDX-33, MDX-CD4, MEDI-507 (Siplizumab), OKT4A, OKT3 (Muromonab-CD3), and ReoPro (Abciximab).

Conjugation Linkers

The conjugate used in the invention may include using any cross-linking (conjugation) reagent or protocol known in the art, many of which are commercially available. Such protocols and reagents include, cross-linkers reactive with amino, carboxyl, sulfhydryl, carbonyl, carbohydrate and/or phenol groups. The amounts, times, and conditions of such protocols can be varied to optimize conjugation. Cross-linking reagents contain at least two reactive groups and are generally divided into homofunctional cross-linkers (containing identical reactive groups) and heterofunctional cross-linkers (containing non-identical reactive groups). The cross-linkers of the invention may be either homobifunctional and/or heterobifunctional. Furthermore the cross-linker may incorporate a 'spacer' between the reactive moieties, or the two reactive moieties in the cross-linker may be directly linked. Bonds may include ester bonds.

Exemplary linkers include $BS^3$ [Bis(sulfosuccinimidyl) suberate], NHS/EDC (N-hydroxysuccinimide and N-ethyl-(dimethylaminopropyl)carbodimide, Sulfo-EMCS ([N-e-Maleimidocaproic acid]hydrazide), SATA (N-succinimidyl-S-acetylthioacetate), and hydrazide. $BS^3$ is a homobifunctional N-hydroxysuccinimide ester that targets accessible primary amines. A conjugation scheme is exemplified in FIG. 2. NHS/EDC allows for the conjugation of primary amine groups with carboxyl groups. Sulfo-EMCS are heterobifunctional reactive groups (maleimide and NHS-ester) that are reactive toward sulfhydryl and amino groups. Amine coupling using sulfo-NHS/EDC activation may be used to cross-link therapeutic antibodies to polypeptides. The resulting conjugate is stable and retains the biological activity of the antibody. Moreover, it has a high conjugation capacity that can be reliably controlled and a low non-specific interaction during coupling procedures. SATA is reactive towards amines and adds protected sulfhydryls groups. The NHS-ester reacts with primary amines to form stable amide bonds. Sulfhydryl groups may be deprotected using hydroxylamine. Hydrazide can be used to link carboxyl groups to primary amines and may therefore be useful for linking glycoproteins.

Small molecules such as therapeutic agents can be conjugated to polypeptides (e.g., those described herein). The exemplary small molecule, paclitaxel, has two strategic positions (position C2' and C7) useful for conjugation. Conjugation of a vector or vector of the invention to paclitaxel can be performed as follows. Briefly, paclitaxel is reacted with anhydride succinic pyridine for three hours at room temperature to attach a succinyl group in position 2'. The 2'-succinyl paclitaxel has a cleavable ester bond in position 2' can simply release succinic acid. This cleavable ester bond can be further used for various modifications with linkers, if desired. The resulting 2'-O-succinyl-paclitaxel is then reacted with EDC/NHS in DMSO for nine hours at room temperature, followed by the addition of the vector or vector in Ringer/DMSO for an additional reaction time of four hours at room temperature. The reaction of conjugation depicted in FIG. 8 is monitored by HPLC. Each intermediate, such as paclitaxel, 2'-O-succinyl-paclitaxel and 2'-O—NHS-succinyl-paclitaxel, is purified and validated using different approaches such as HPLC, thin liquid chromatography, NMR ($^{13}$C or $^{1}$H exchange), melting point, mass spectrometry. The final conjugate is analyzed by mass spectrometry and SDS-polyacrylamide gel electrophoresis. This allows determining the number of paclitaxel molecules conjugated on each vector.

Dosages

The dosage of any conjugate or composition described herein depends on several factors, including: the administration method, the severity of the disease, whether the cancer is to be treated or prevented, and the age, weight, and health of the subject to be treated.

With respect to the treatment methods of the invention, it is not intended that the administration of a vector, conjugate, or composition to a subject be limited to a particular mode of administration, dosage, or frequency of dosing; the invention contemplates all modes of administration. The conjugate, or composition may be administered to the subject in a single dose or in multiple doses. For example, a compound described herein or identified using screening methods of the invention may conjugate be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the composition. For example, the dosage of a composition can be increased if the lower dose does not provide sufficient activity in the treatment of a disease or condition described herein (e.g., cancer). Conversely, the dosage of the composition can be decreased if the disease (e.g., cancer) is reduced or eliminated.

While the attending physician ultimately will decide the appropriate amount and dosage regimen, a therapeutically effective amount of a vector, conjugate, or composition described herein, may be, for example, in the range of 0.0035 µg to 20 µg/kg body weight/day or 0.010 µg to 140 µg/kg body weight/week. Desirably a therapeutically effective amount is in the range of 0.025 µg to 10 µg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of 0.05 µg to 20 µg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, every three weeks or once a month. Furthermore, a therapeutically effective amount of a compound may be, for example, in the range of 0.1 mg/m$^2$ to 2,000 mg/m$^2$ administered every other day, once weekly, every other week or every three weeks. For example ANG1005, may be administered at 50, 100, 200, 300, 400, 420, 500, 600, 650, 700, 800, or 1,000 mg/m$^2$ every one, two, three, four weeks, or every month or every other month. In one particular example, ANG1005 is administered at 300 mg/m$^2$ or 420 mg/m$^2$ every three weeks. In another embodiment, the therapeutically effective amount is in the range of 1000 µg/m$^2$ to 20,000 µg/m$^2$, for example, at least 1000, 1500, 4000, or 14,000 µg/m$^2$ of the compound administered daily, every other day, twice weekly, weekly, or every other week.

Formulation of Pharmaceutical Compositions

The administration of a conjugate described herein or a composition containing the conjugate may be by any suitable means that results in a concentration of the compound that treats ovarian cancer. The conjugate may be in any appropriate amount of any suitable carrier substance, and is generally present in an amount of 1-95% by weight of the total weight of the composition. The composition may be provided in a dosage form that is suitable for the oral, parenteral (e.g., intravenously or intramuscularly), rectal, cutaneous, nasal, vaginal, inhalant, skin (patch), topical, ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions may be formulated to release the conjugate(s) immediately upon administration or at any predetermined time or time period after administration. The latter types of compositions are generally known as controlled release formulations, which include (i) formulations that create substantially constant concentrations of the conjugate(s) within the body over an extended period of time; (ii) formulations that after a predetermined lag time create substantially constant concentrations of the conjugate(s) within the body over an extended period of time; (iii) formulations that sustain the conjugate(s) action during a predetermined time period by maintaining a relatively constant, effective level of the conjugate(s) in the body with concomitant minimization of undesirable side effects associated with fluctuations in the plasma level of the conjugate(s) (sawtooth kinetic pattern); (iv) formulations that localize action of conjugate(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the conjugate(s) by using carriers or chemical derivatives to deliver the compound to a particular target cell type. Administration of the conjugate(s) in the form of a controlled release formulation is especially preferred for conjugate(s) having a narrow absorption window in the gastro-intestinal tract or a relatively short biological half-life.

Any of a number of strategies can be pursued in order to obtain controlled release in which the rate of release outweighs the rate of metabolism of the conjugate(s) in question. In one example, controlled release is obtained by appropriate selection of various formulation parameters and ingredients, including, e.g., various types of controlled release compositions and coatings. Thus, the conjugate(s) is formulated with appropriate excipients into a pharmaceutical composition that, upon administration, releases the conjugate(s) in a controlled manner. Examples include single or multiple unit tablet or capsule compositions, oil solutions, suspensions, emulsions, microcapsules, molecular complexes, microspheres, nanoparticles, patches, and liposomes.

Formulation of Pharmaceutical Compositions

The administration of a conjugate described herein or a composition containing the conjugate may be by any suitable means that results in a concentration of the compound that treats ovarian cancer. The conjugate may be in any appropriate amount of any suitable carrier substance, and is generally present in an amount of 1-95% by weight of the total weight of the composition. The composition may be provided in a dosage form that is suitable for the oral, parenteral (e.g., intravenously or intramuscularly), rectal, cutaneous, nasal, vaginal, inhalant, skin (patch), topical, ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions may be formulated to release the conjugate(s) immediately upon administration or at any predetermined time or time period after administration. The latter types of compositions are generally known as controlled release formulations, which include (i) formulations that create substantially constant concentrations of the conjugate(s) within the body over an extended period of time; (ii) formulations that after a predetermined lag time create substantially constant concentrations of the conjugate(s) within the body over an extended period of time; (iii) formulations that sustain the conjugate(s) action during a predetermined time period by maintaining a relatively constant, effective level of the conjugate(s) in the body with concomitant minimization of undesirable side effects associated with fluctuations in the plasma level of the conjugate(s) (sawtooth kinetic pattern); (iv) formulations that localize action of conjugate(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the conjugate(s) by using carriers or chemical derivatives to deliver the compound to a particular target cell type. Administration of the conjugate(s) in the form of a controlled release formulation is especially preferred for conjugate(s) having a narrow absorption window in the gastro-intestinal tract or a relatively short biological half-life.

Any of a number of strategies can be pursued in order to obtain controlled release in which the rate of release outweighs the rate of metabolism of the conjugate(s) in question. In one example, controlled release is obtained by appropriate selection of various formulation parameters and ingredients, including, e.g., various types of controlled release compositions and coatings. Thus, the conjugate(s) is formulated with appropriate excipients into a pharmaceutical composition that, upon administration, releases the conjugate(s) in a controlled manner. Examples include single or multiple unit tablet or capsule compositions, oil solutions, suspensions, emulsions, microcapsules, molecular complexes, microspheres, nanoparticles, patches, and liposomes.

Other Embodiments

All patents, patent applications, and publications mentioned in this specification are herein incorporated by reference to the same extent as if each independent patent, patent application, or publication was specifically and individually indicated to be incorporated by reference.

What is claimed is:

1. A method of treating a patient having metastatic ovarian cancer after failure of a prior chemotherapy that comprised a taxane, said method comprising administering to said patient an effective amount of ANG1005 which has the structure:

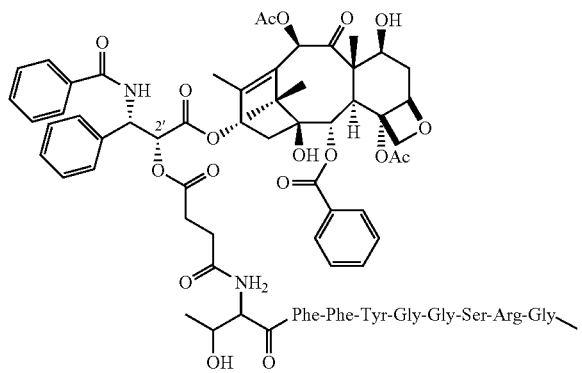

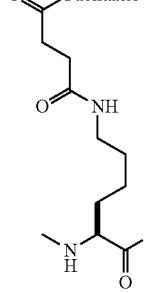

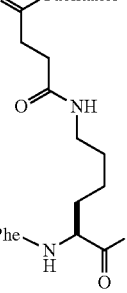

2. The method of claim 1, wherein said conjugate is administered in a dosage of between 100 mg/m$^2$ and 2000 mg/m$^2$.

3. The method of claim 2, wherein said conjugate is administered in a dosage of between 300 mg/m$^2$ and 1000 mg/m$^2$.

4. The method of claim 1, wherein said conjugate is administered intravenously.

5. The method of claim 1, wherein said cancer has metastasized to at least one location outside the brain of said patient.

6. The method of claim 1, wherein said cancer has metastasized outside the pelvis of said patient.

7. The method of claim 1, wherein said cancer has metastasized to the brain, lung, liver, or a combination thereof.

8. The method of claim 1, wherein said cancer has metastasized into the lymph system.

9. The method of claim 1, wherein said cancer comprises cancer cells that express MDR1.

10. The method of claim 1, wherein said cancer comprises cancer cells that are resistant to paclitaxel treatment or to treatment with a taxane derivative.

11. The method of claim 1, wherein said method further includes administration of a second anticancer therapy.

12. The method of claim 1, wherein said prior chemotherapy comprised paclitaxel, a platinum-based agent, an alkylating agent, or a combination thereof.

13. The method of claim 12, wherein said platinum-based agent is carboplatin or cisplatin.

14. The method of claim 12, wherein said patient previously received combination carboplatin-paclitaxel therapy.

15. The method of claim 1, wherein said cancer is an ovarian epithelial carcinoma or ovarian adenocarcinoma.

16. The method of claim 1, wherein ANG1005 is administered every three weeks.

* * * * *

SEQUENCE LISTING

```
<160> NUMBER OF SEQ ID NOS: 116

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
```

<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Thr Phe Phe Tyr Gly Gly Cys Leu Gly Lys Gly Asn Asn Phe Leu Thr
1               5                   10                  15

Ala Lys Tyr

```
<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Asn Tyr Val Arg
1               5                   10                  15

Glu Lys Tyr
```

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

```
<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57
```

Thr Phe Phe Tyr Gly Gly Cys Leu Gly Lys Gly Asn Asn Phe Val Ser
1               5                   10                  15

Ala Glu Tyr

```
<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58
```

Thr Phe Phe Tyr Gly Gly Cys Leu Gly Asn Arg Asn Asn Phe Asp Arg
1               5                   10                  15

Ala Glu Tyr

```
<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59
```

Thr Phe Phe Tyr Gly Gly Cys Leu Gly Asn Arg Asn Asn Phe Leu Arg
1               5                   10                  15

Glu Glu Tyr

```
<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

Thr Phe Phe Tyr Gly Gly Cys Leu Gly Asn Lys Asn Asn Tyr Leu Arg
1               5                   10                  15

Glu Glu Tyr

```
<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

Pro Phe Phe Tyr Gly Gly Cys Gly Gly Asn Arg Asn Asn Tyr Leu Arg

```
1               5                   10                  15
Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Phe Phe Tyr Gly Gly Lys Arg Gly Lys Arg Asn Asn Phe Lys Thr
1               5                   10                  15

Ala Gly Tyr
```

```
<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr
```

```
<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Phe Lys Tyr Gly Gly Cys Leu Gly Asn Lys Asn Asn Phe Leu Arg
1               5                   10                  15

Leu Lys Tyr
```

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
1               5                   10

```
<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100
```

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
                20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
                20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
                20

<210> SEQ ID NO 105
<211> LENGTH: 20
<212> TYPE: PRT

<213> ORGANISM: Artificial Sequence
<220> FEATURE:
<223> OTHER INFORMATION: Description of Artificial Sequence: Synthetic peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106
atgagaccag atttctgcct cgagccgccg tacactgggc cctgcaaagc tcgtatcatc      60
cgttacttct acaatgcaaa ggcaggcctg tgtcagacct tcgtatacgg cggctgcaga     120
gctaagcgta acaacttcaa atccgcggaa gactgcatgc gtacttgcgg tggtgcttag     180

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: ACETYLATION

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: ACETYLATION

```
<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION

<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Phe Phe Tyr Gly Gly Ser Arg Gly Arg Arg Asn Asn Phe Arg Thr
1               5                   10                  15

Glu Glu Tyr Cys
            20
```